United States Patent [19]

Sprecker et al.

[11] 4,391,284
[45] Jul. 5, 1983

[54] USE IN MODIFYING SMOKING TOBACCO AROMA AND FLAVOR OR MONO-OXOMETHYL SUBSTITUTED POLYHYDRODIMETHANONAPHTHALENE DERIVATIVES

[75] Inventors: Mark A. Sprecker, Sea Bright; Marie R. Hanna, Hazlet; Richard J. Tokarzewski, Keyport; Robert P. Belko, Woodbridge; Hugh Watkins, Lincroft; Manfred H. Vock, Locust, all of N.J.

[73] Assignee: International Flavors & Fragrances Inc., New York, N.Y.

[21] Appl. No.: 354,387

[22] Filed: Mar. 2, 1982

[51] Int. Cl.$^3$ .................. A24B 3/12; A24B 15/30
[52] U.S. Cl. ................................. 131/276; 131/277
[58] Field of Search .............................. 131/271–278

Primary Examiner—V. Millin
Attorney, Agent, or Firm—Arthur L. Liberman

[57] ABSTRACT

Described is the use in modifying, augmenting or enhancing the aroma or taste of smoking tobacco products of mono-oxomethyl substituted polyhydrodimethanonaphthalene derivatives having the generic structure:

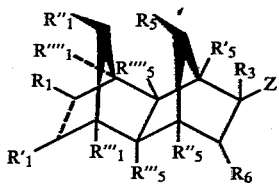

wherein the dashed line represents a carbon-carbon single bond or a carbon-carbon double bond; wherein $R_1$, $R_1'$, $R_1''$, $R_1'''$, $R_1''''$, $R_3$, $R_5$, $R_5'$, $R_5''$, $R_5'''$, $R_5''''$ and $R_6$ represent hydrogen or methyl with the provisos:
  (i) at least four of $R_1$, $R_1'$, $R_1''$, $R_1'''$ and $R_1''''$ are hydrogen; and (ii) at least four of $R_5$, $R_5'$, $R_5''$, $R_5'''$ and $R_5''''$ represent hydrogen;

and wherein Z represents one of the moieties:
(i) carboxaldehyde having the structure:

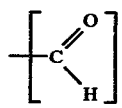

(ii) alkylene dioxy or dialkoxy methyl having the structure:

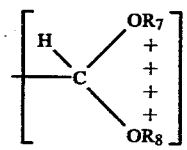

(iii) hydroxy methyl having the structure:

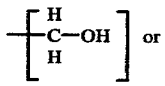

or (iv) acetoxymethyl having the structure:

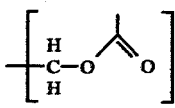

and wherein $R_7$ and $R_8$ taken separately represent $C_1$–$C_4$ lower alkyl or $R_7$ and $R_8$ taken together represent $C_2$–$C_4$ alkylene: wherein the line represented by:

[++++]

is either (i) a carbon-carbon single bond when $R_7$ and $R_8$ taken together are $C_2$–$C_4$ alkylene or (ii) no bond at all when $R_7$ and $R_8$ taken separately represent $C_1$–$C_4$ lower alkyl.

10 Claims, 29 Drawing Figures

GLC PROFILE FOR EXAMPLE I.

GLC PROFILE FOR EXAMPLE I.

FIG. 2 NMR SPECTRUM FOR FRACTION II OF EXAMPLE II.

IR SPECTRUM FOR EXAMPLE I

GLC PROFILE FOR EXAMPLE II.

IR SPECTRUM FOR FRACTION 2 OF EXAMPLE II

GLC PROFILE FOR BULKED FRACTIONS FOR EXAMPLE IV.

GLC PROFILE FOR EXAMPLE III.

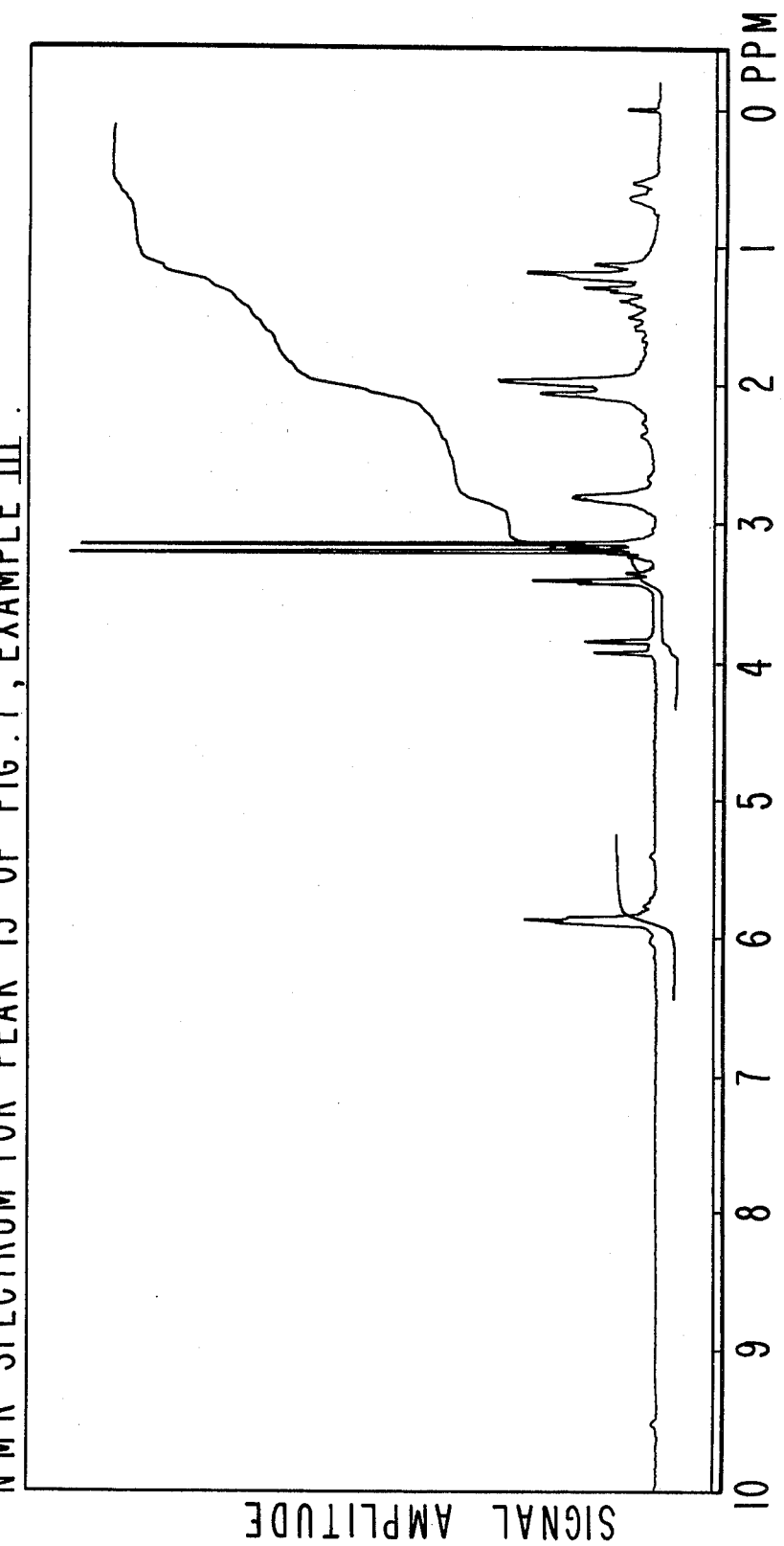
FIG. 8 NMR SPECTRUM FOR PEAK 13 OF FIG. 7, EXAMPLE III

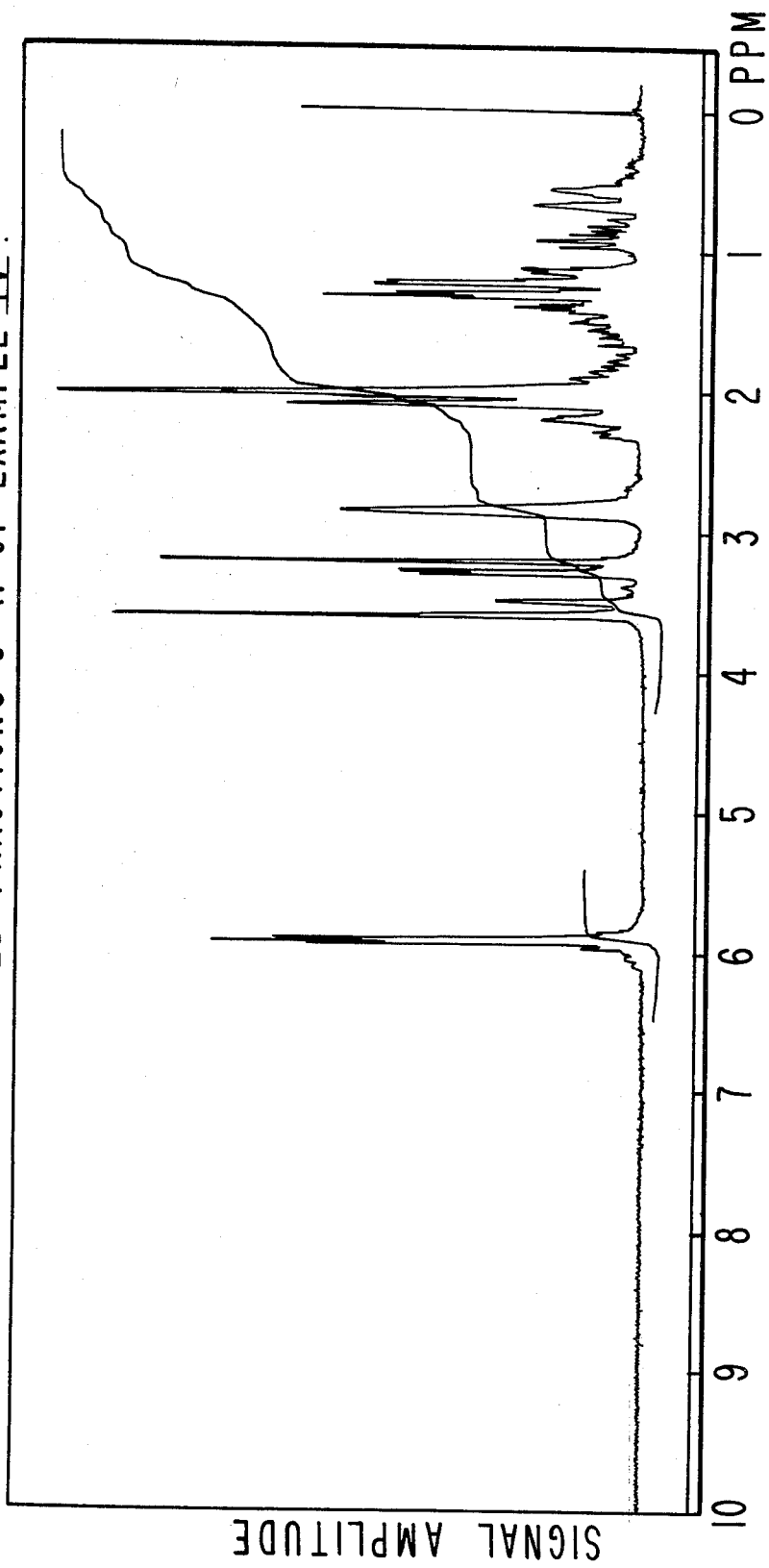

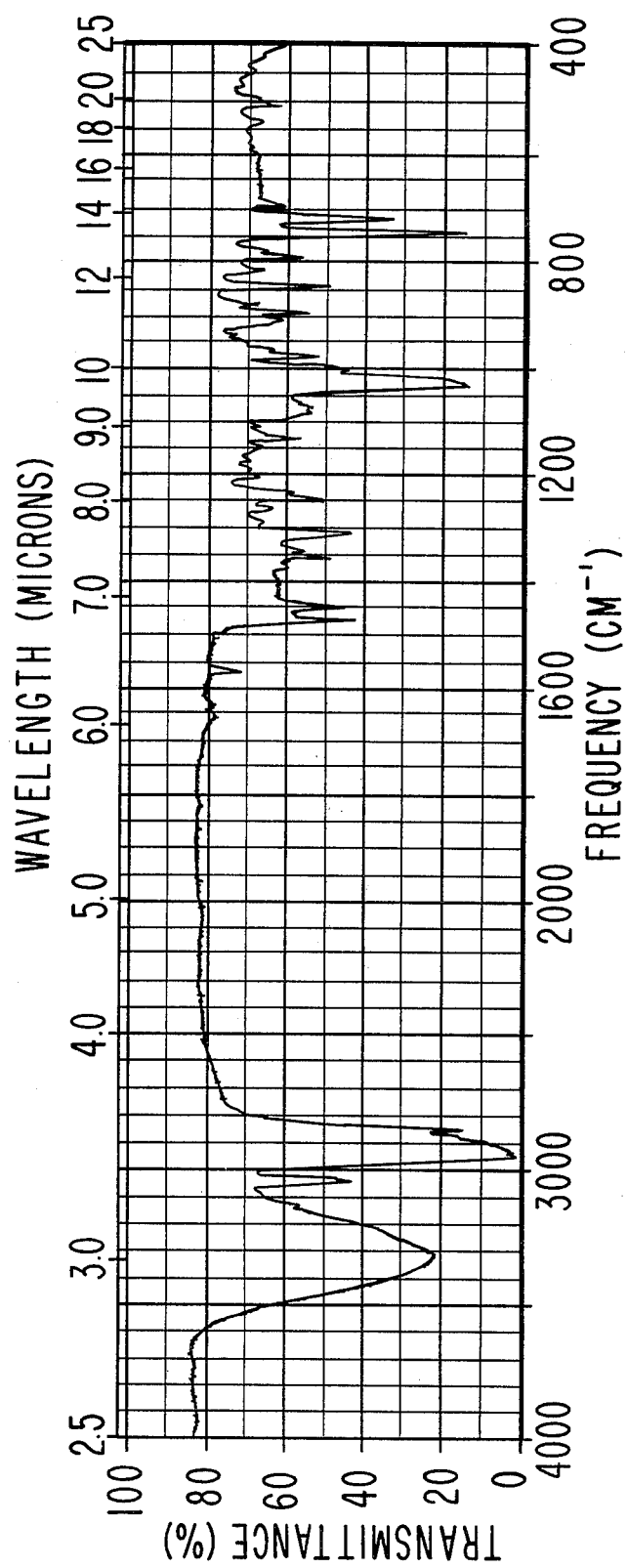
FIG. II
IR SPECTRUM FOR BULKED FRACTIONS 3 TO 11 OF EXAMPLE IV.

GLC PROFILE FOR EXAMPLE VI.

GLC PROFILE FOR EXAMPLE V.

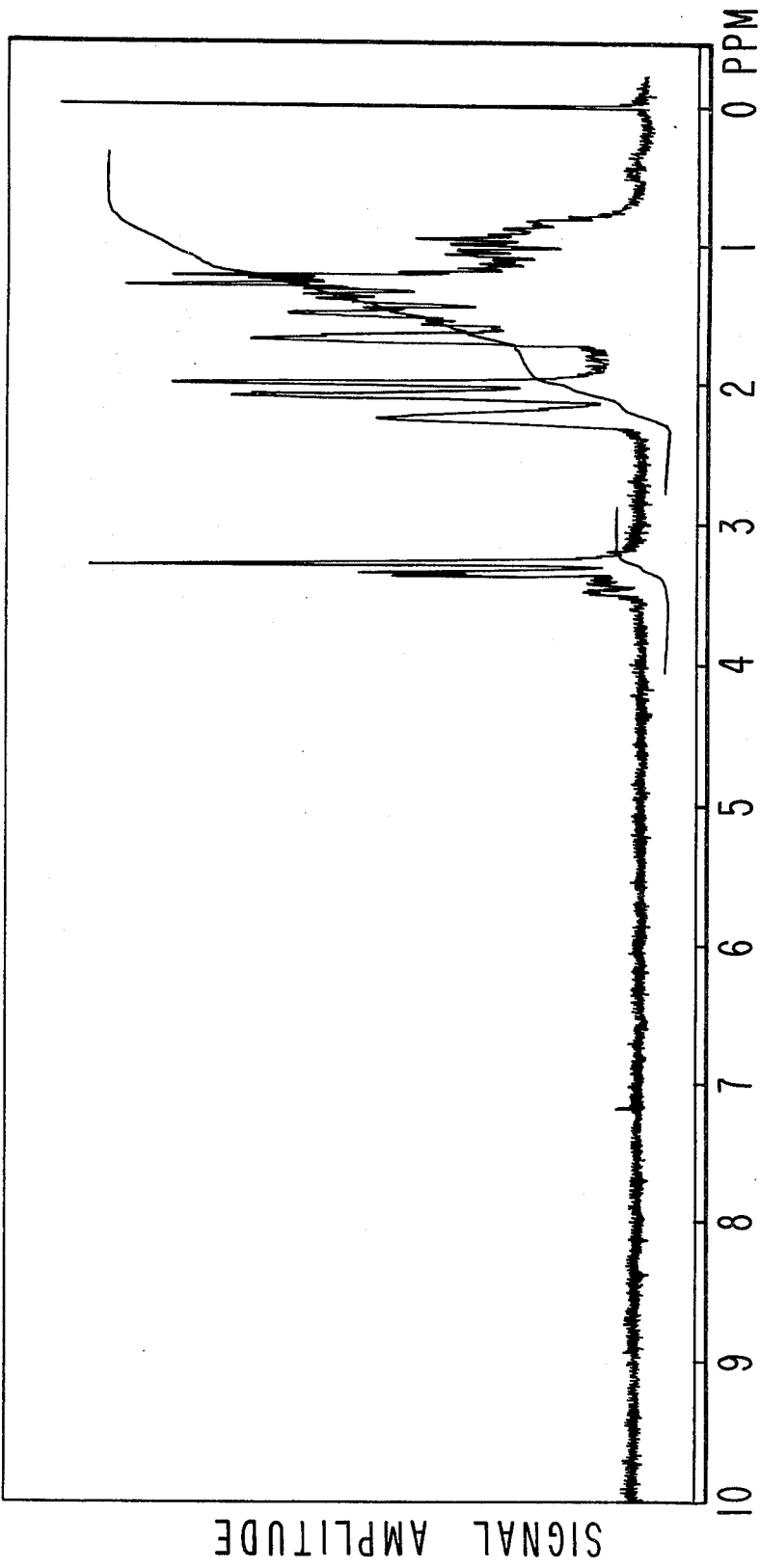
FIG. 13 NMR SPECTRUM FOR FRACTION 8 OF EXAMPLE V.

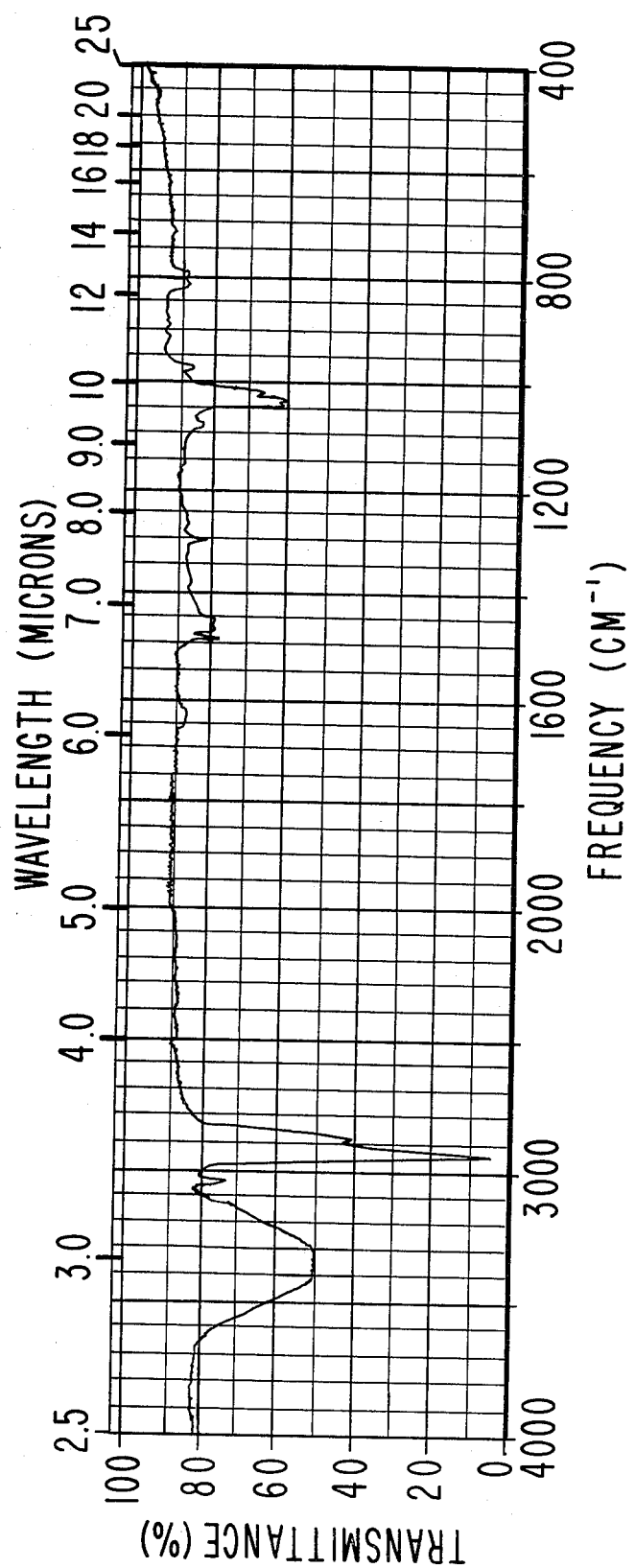

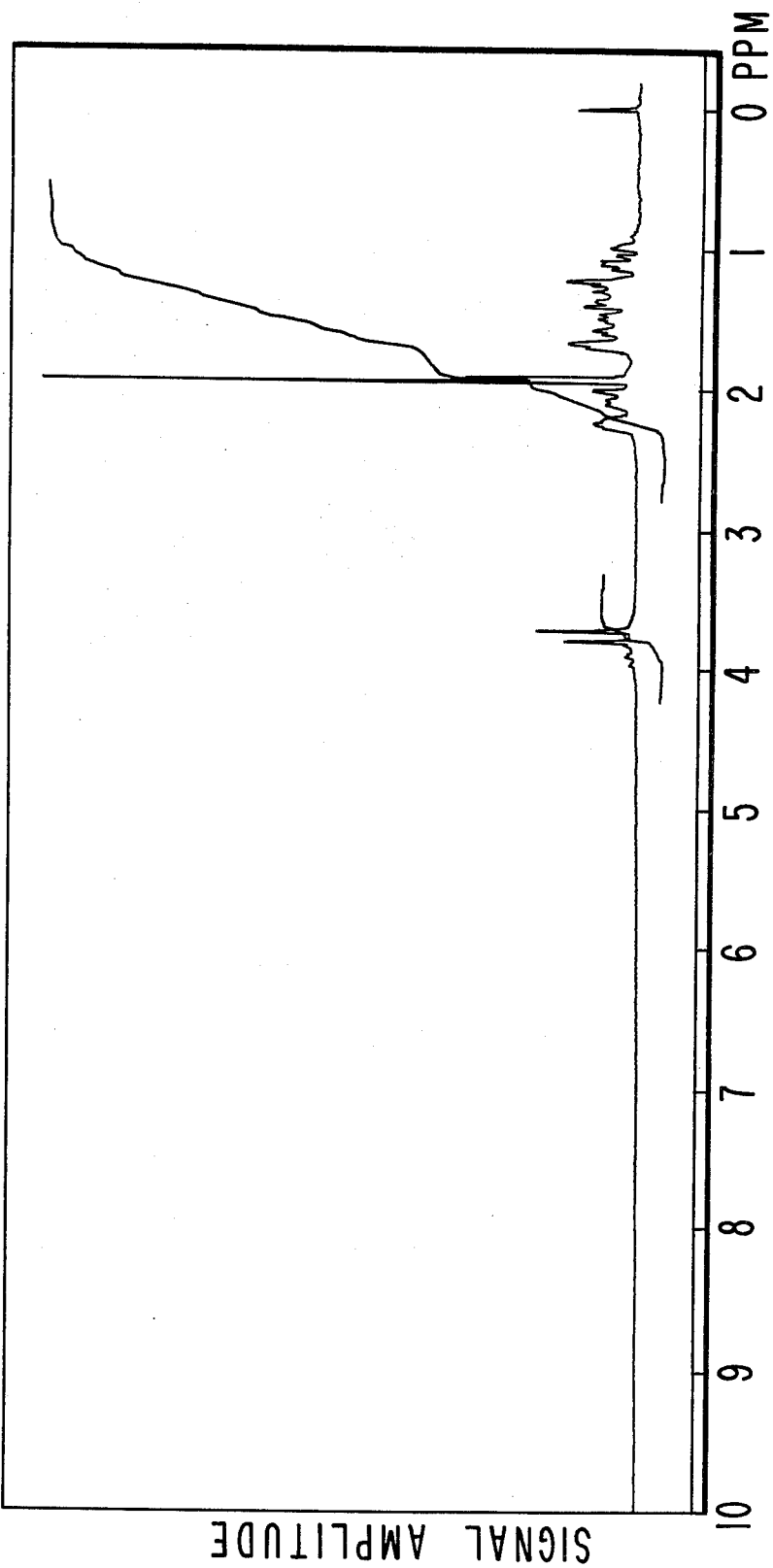
FIG. 16 NMR SPECTRUM FOR FRACTION 6 OF EXAMPLE VI.

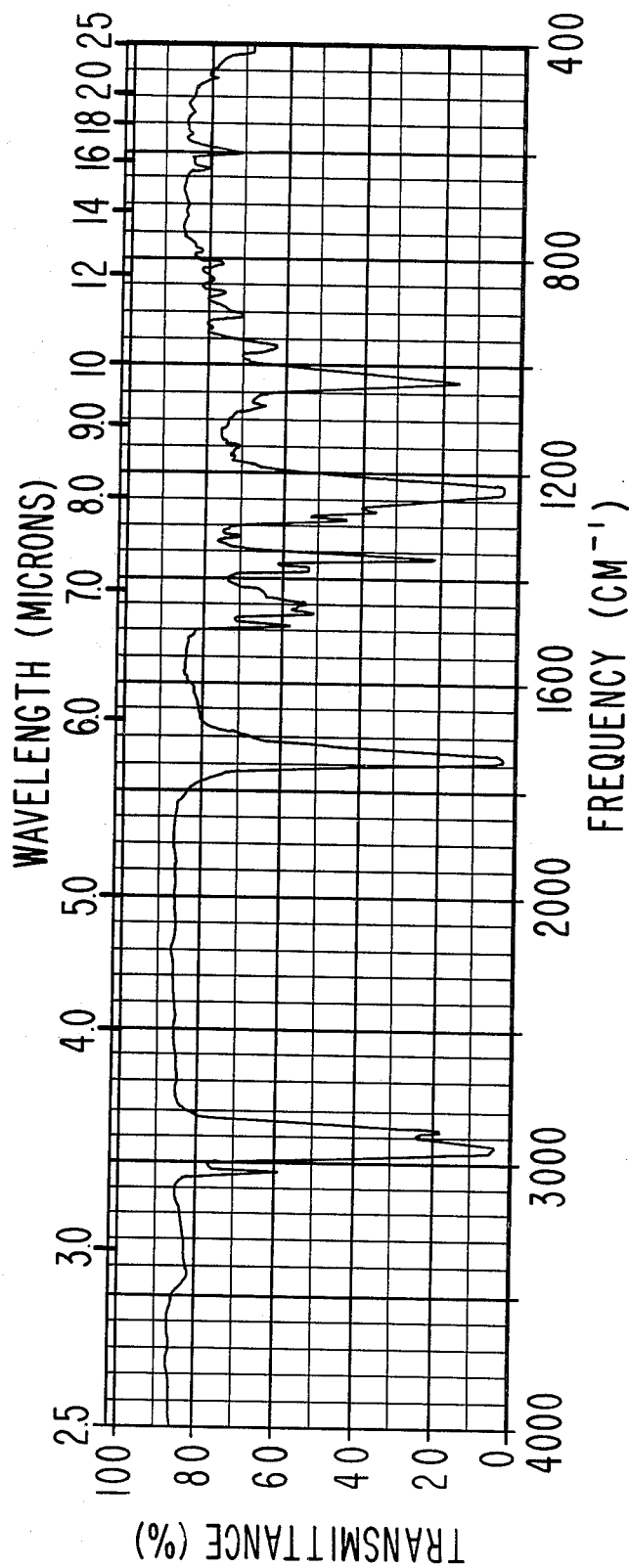

GLC PROFILE FOR EXAMPLE VIII.

GLC PROFILE FOR EXAMPLE VII.

FIG.19 NMR SPECTRUM FOR FRACTION 4 OF EXAMPLE VII.

IR SPECTRUM FOR FRACTION 4 OF EXAMPLE VII

NMR SPECTRUM FOR PEAK 51 OF FIG. 21, EXAMPLE VIII.

IR SPECTRUM FOR PEAK 51 OF FIG. 21, EXAMPLE VIII.

GLC PROFILE FOR EXAMPLE X.

GLC PROFILE FOR EXAMPLE IX

NMR SPECTRUM FOR EXAMPLE IX

IR SPECTRUM FOR EXAMPLE IX.

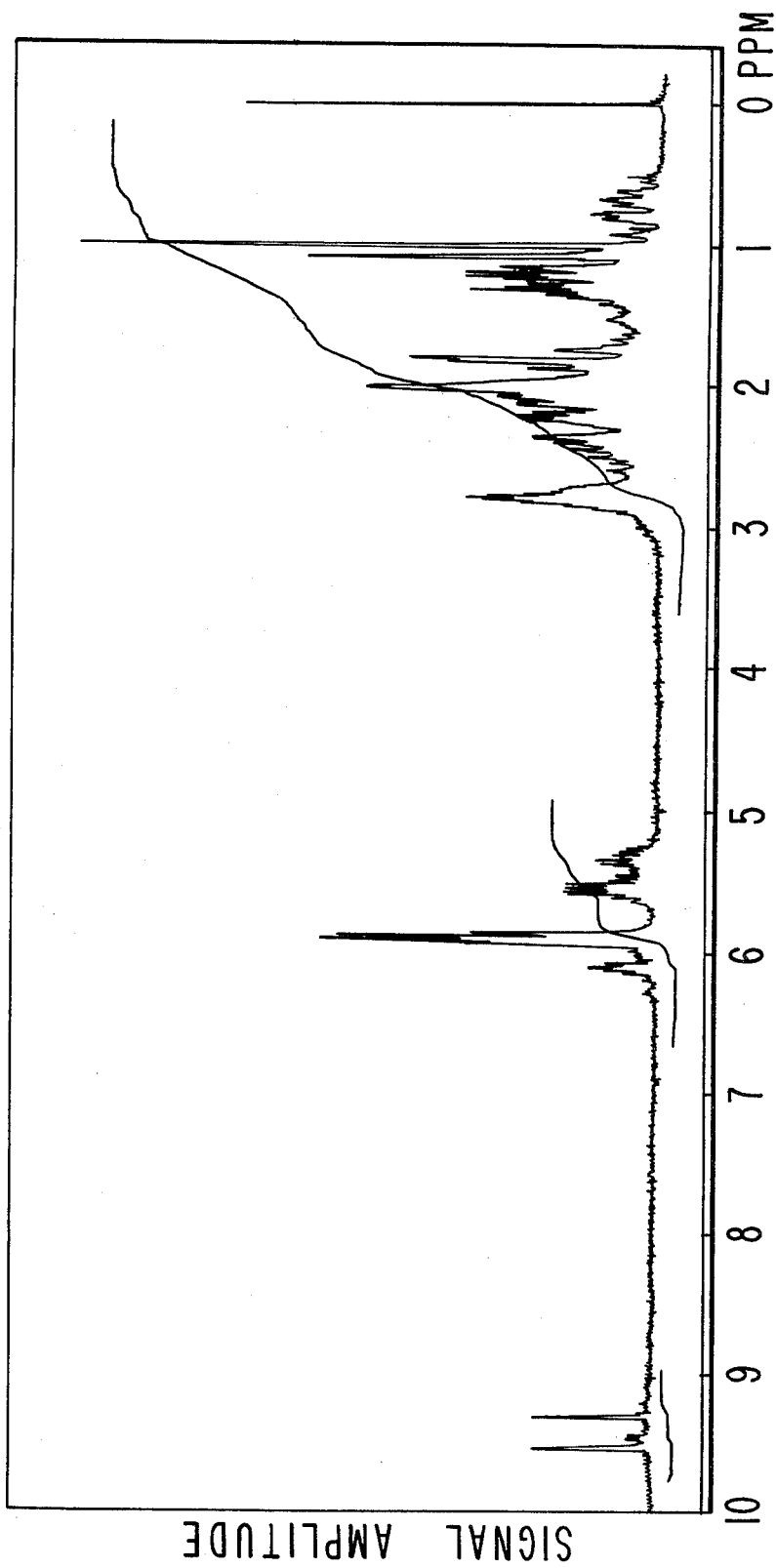

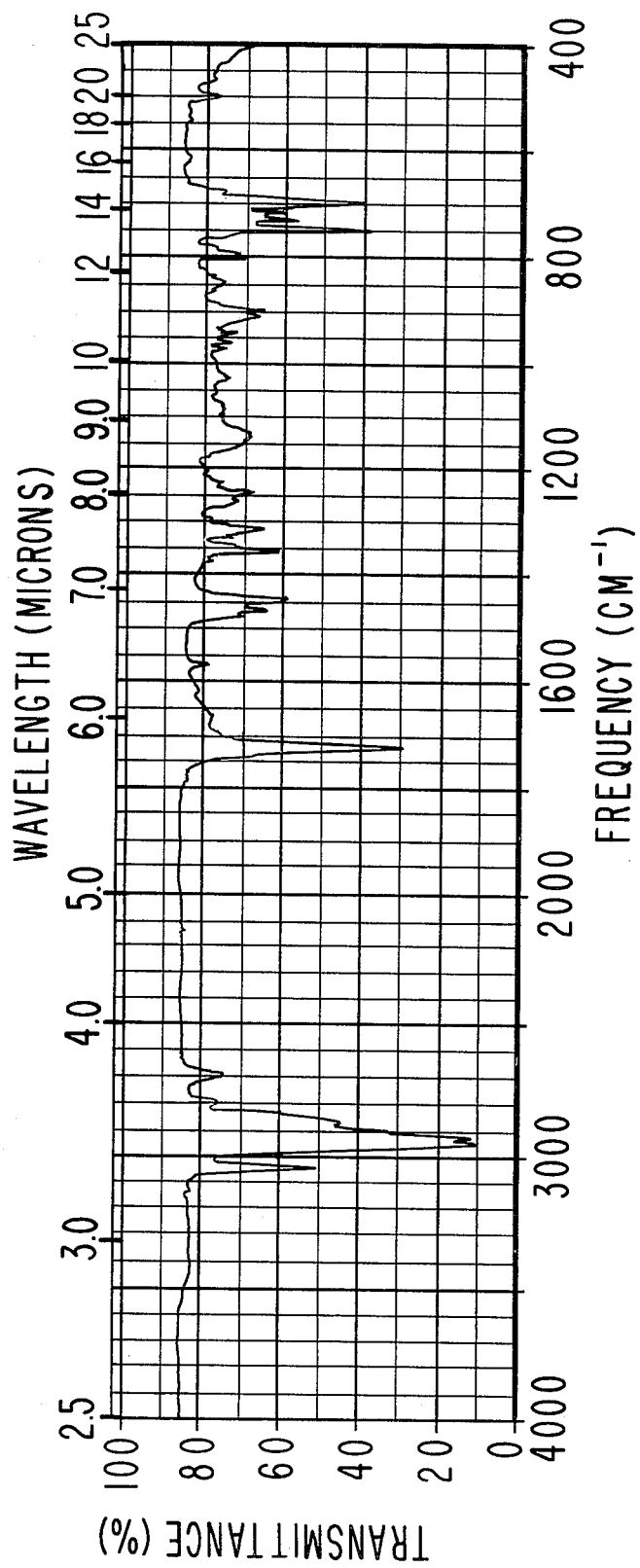
FIG. 29 — IR SPECTRUM FOR EXAMPLE X

USE IN MODIFYING SMOKING TOBACCO AROMA AND FLAVOR OR MONO-OXOMETHYL SUBSTITUTED POLYHYDRODIMETHANONAPHTHALENE DERIVATIVES

BACKGROUND OF THE INVENTION

Materials including mixtures of natural products which can provide, augment or enhance melony, cucumber, violet-like, green, leafy green, herbaceous, wormwood-like, floral, cinnamic, sandalwood-like, patchouli-like, vetiver-like, sweaty, animalic and spicy fragrance notes are known in the art of perfumery. Many of the natural materials which provide such fragrances and contribute desired nuances to perfumery compositions are high in cost, vary in quality from one batch to another and/or are generally subject to the usual variations in the natural products.

There is, accordingly, a continuing effort to find synthetic materials which will replace the essential fragrance notes provided by such natural essential oils or compositions thereof. Unfortunately, many of these synthetic materials either have the desired nuances only to a relatively small degree or else contribute undesirable or unwanted odor to the perfume compositions, perfumed articles or colognes using the same. The search for materials which can provide a more refined patchouli-like fragrance, for example, or a more refined floral fragrance, for example, or combination thereof ("floral/patchouli") has been difficult and relatively costly in the areas of both natural products and synthetic products.

In addition, artificial flavoring agents for foodstuffs have received increasing attention in recent years. For many years, such food flavoring agents have been preferred over natural flavoring agents at least in part due to their diminished costs and their reproducible flavor qualities. For example, natural food flavoring agents such as extracts, concentrates and the like are often subject to wide variations due to changes in quality, and type and treatment of the raw materials. Such variations can be reflected in the end product and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods is not completely known. This is noticeable in products which have orange flavors, mint flavors, peppermint flavors, and even artichoke-like flavors and corresponding aroma characteristics.

Thus, reproduction of sweet, aldehydic, floral, melony, herbaceous, green, and artichoke-like aroma and taste characteristics has been the subject of long and continuing searches by those engaged in the production of foodstuffs and beverages. The severe shortage of food in many parts of the world has given rise to the development of previously unused sources of protein which have heretofore been unpalatable. Accordingly, the need has arisen for the use of flavoring materials which will make such sources of protein palatable to human sensory organs.

The use of tricyclohydrocarbyl oxomethyl derivatives is known in the art of perfumery. Thus, U.S. Pat. No. 4,123,394 issued on Oct. 31, 1978 discloses specifically the compound having the structure:

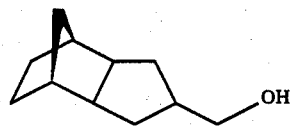

and generically the compound having the structure:

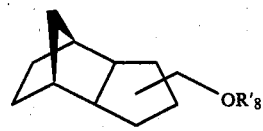

wherein $R_8'$ is hydrogen, acyl, alkyl or alkenyl.

French Pat. No. 2,424,244 (corresponding to British Patent Application No. 2,019,841) discloses 8-exo-hydroxymethyl-endo-tricyclodecanes useful as perfumery agents in soaps, shampoos, cosmetics and waxes wherein the fragrances range from green, green grass-like, fruit-like to wood-like. The generic structure of the compounds disclosed in French Pat. No. 2,424,244 (assigned to the Kao Soap Company of Japan) is:

wherein R is unsaturated $C_1$–$C_5$ alkyl, $C_1$–$C_5$ acyl or glycidyl and the esters are prepared from the compound wherein R is hydrogen by means of esterification with a carboxylic acid and a mineral acid catalyst and ethers are prepared from the compound wherein R equals H using a sodium hydride/alkyl iodide compound and the glycidyl ethers are prepared from allyl ethers by treatment with peracids.

A number of the aldehydes found to be useful in our invention are known in the prior art.

Thus, Japanese Patent No. J76-011625 of April 1976 (assigned to Nado Research Institute Company) discloses a genus of compounds defined according to the structure:

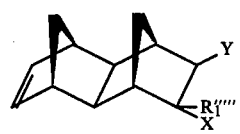

wherein $R_1''''$ represents hydrogen, alkyl, or one of the moieties:

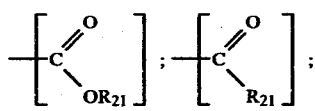

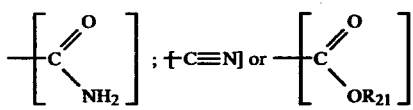

and R₂₁ is hydrogen or alkyl; and wherein Y represents hydrogen, alkyl or one of the moieties:

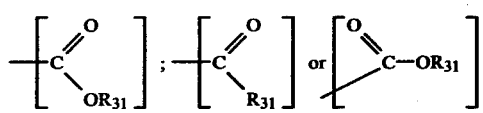

wherein $R_{31}$ represents hydrogen or alkyl.

In addition, Japanese Patent No. J75-135071 abstracted at Vol. 84, Chem. Abstracts 43466h discloses the compound having the structure:

and Chem. Abstract Vol. 60, 4026g (1964) (Abstract of Compt. Rend. 257 (20) 2995-8 (1963) discloses the compound having the structure:

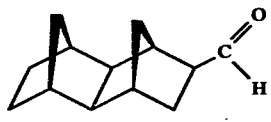

None of the references disclosing the foregoing tetracyclic carboxaldehydes discloses their utilization for augmenting or enhancing the aroma or taste of consumable materials.

In addition, nothing in the prior art discloses the other compounds of our invention or organoleptic utilities of any mono-oxomethyl substituted polyhydrodimethanonaphthalene derivatives.

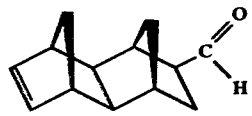

Figure 2:
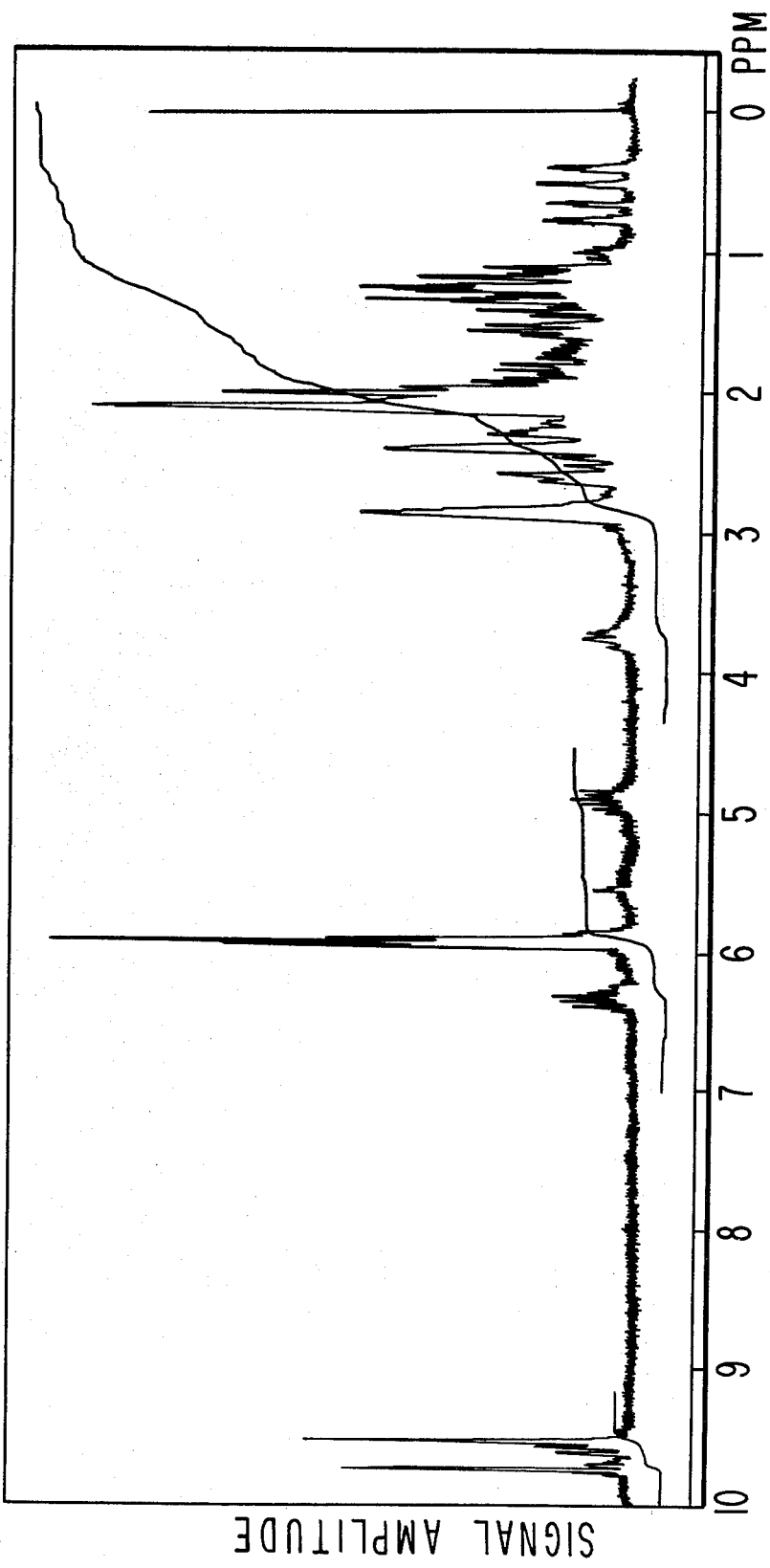

FIG. 2 is the NMR spectrum for the reaction product of Example I containing the compound having the structure:

Figure 3:
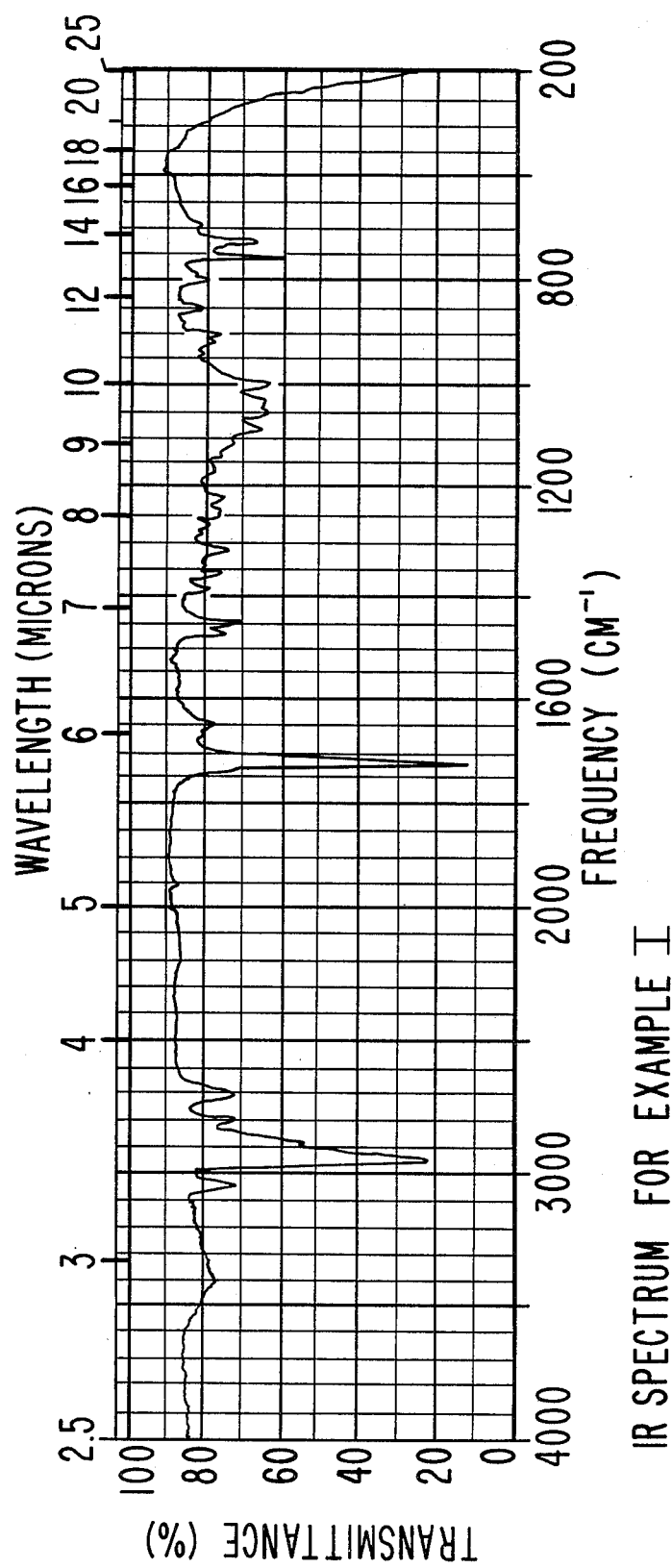

FIG. 3 is the infra-red spectrum for the reaction product of Example I containing the compound having the structure:

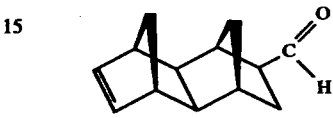

Figure 4:
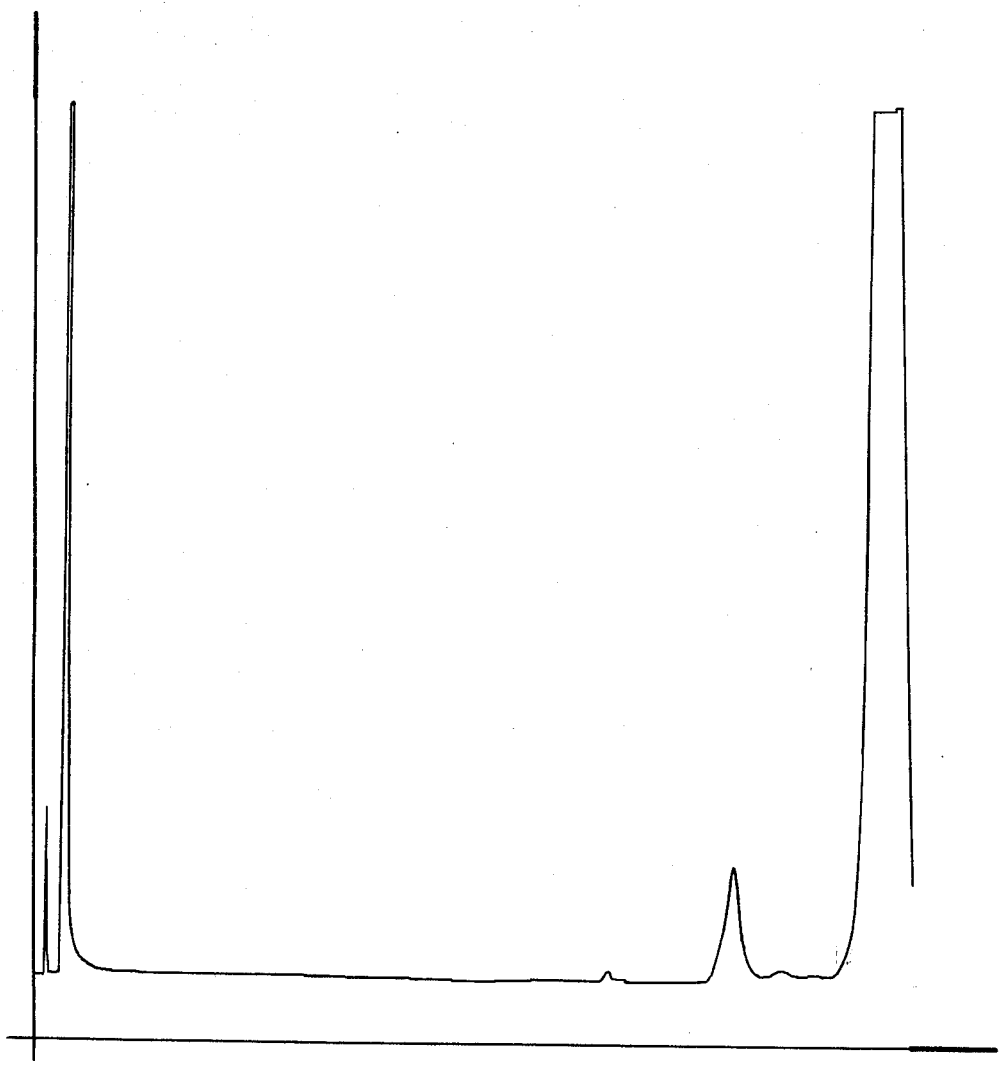

FIG. 4 is the GLC profile for the reaction product of Example II containing the compound having the structure:

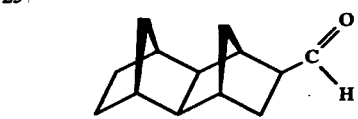

Figure 5:
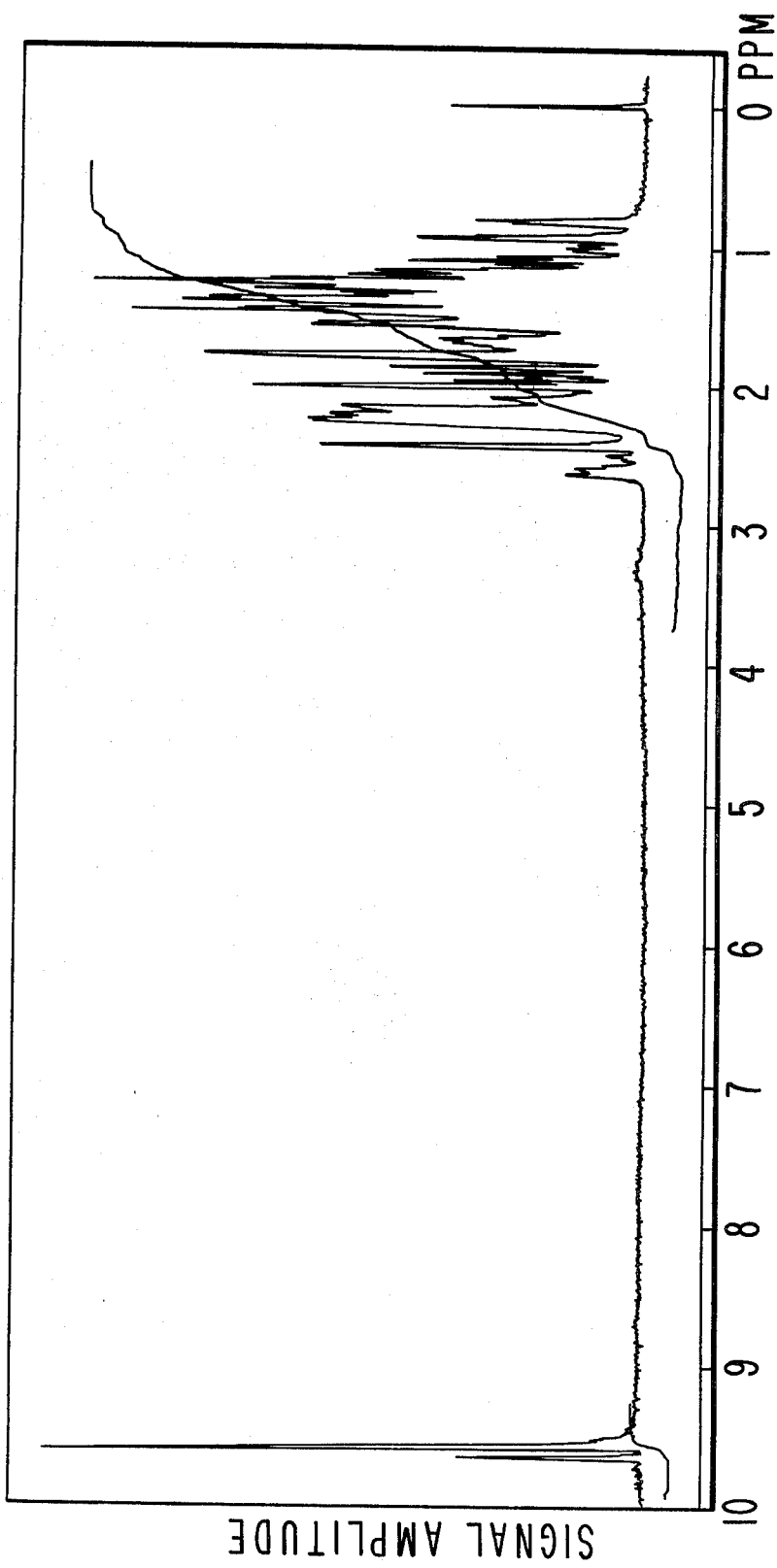

FIG. 5 is the NMR spectrum for fraction 11 of the distillation product of the reaction product of Example II containing the compound having the structure:

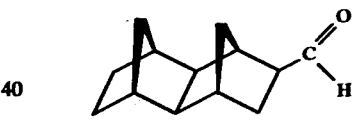

Figure 6:
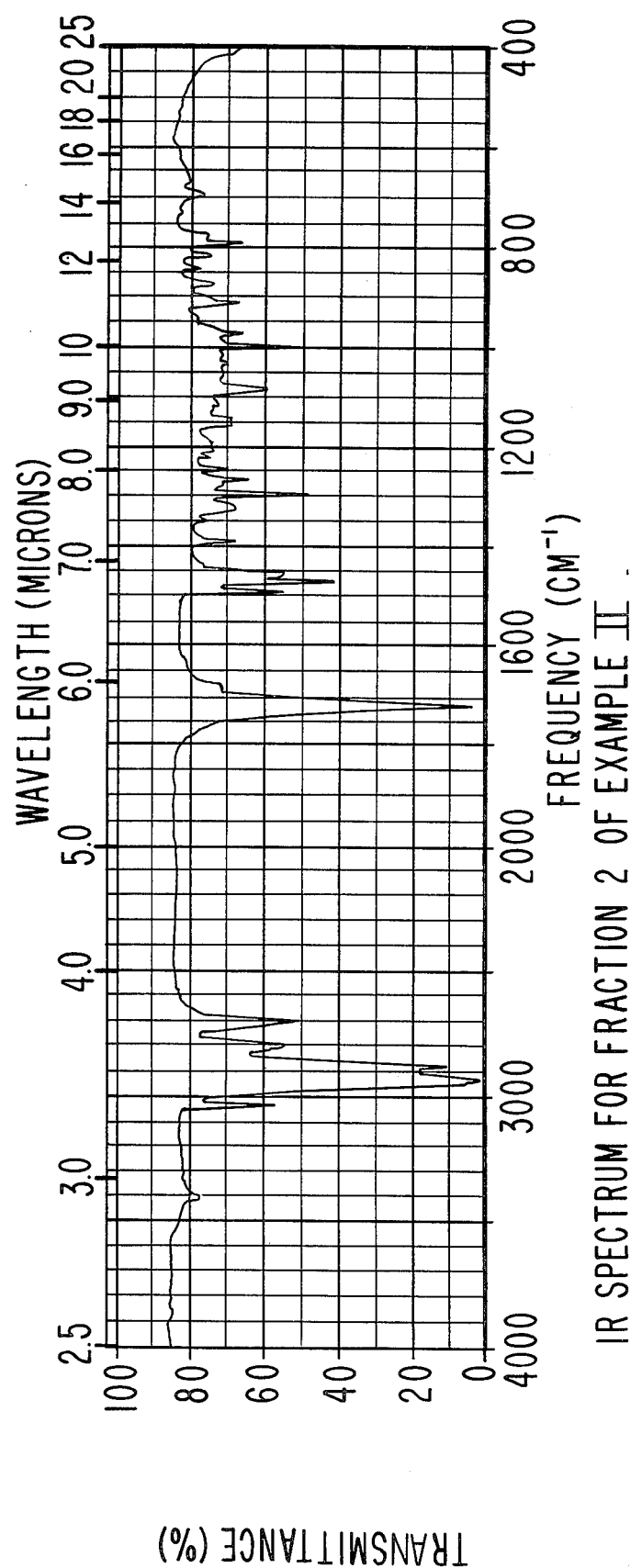

FIG. 6 is the infra-red spectrum for fraction 11 of the distillation product of the reaction product of Example II containing the compound having the structure:

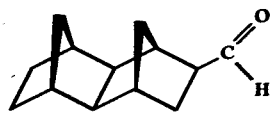

Figure 7:
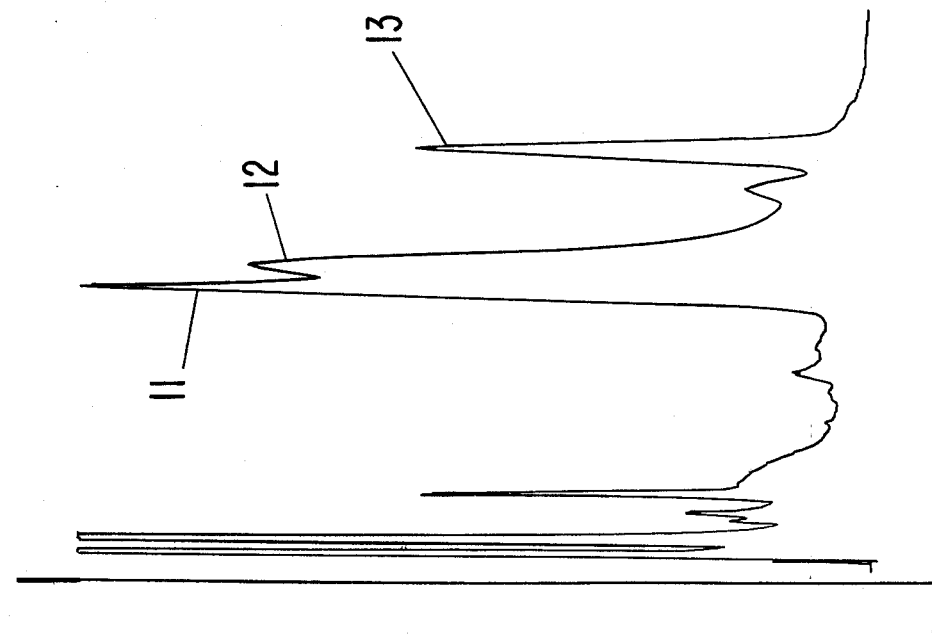

FIG. 7 is the GLC profile for the reaction product of Example III containing the compound having the structure:

FIG. 8 is the NMR spectrum for Peak 13 of the GLC profile of FIG. 7 for the reaction product of Example III containing the compound having the structure:

Figure 9:
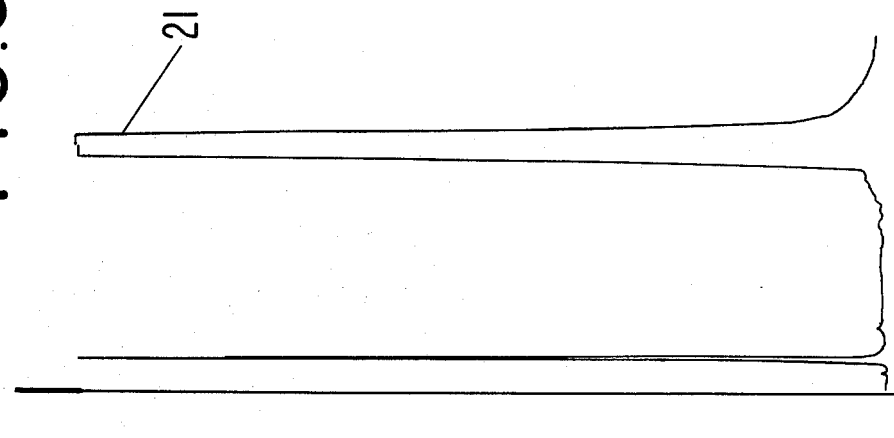

FIG. 9 is the GLC profile for bulked fractions 3-11 of the distillation product of the reaction product of Example IV containing the compound having the structure:

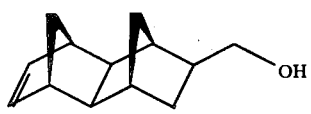

FIG. 10 is the NMR spectrum for bulked fractions 3-11 of the distillation product of the reaction product of Example IV containing the compound having the structure:

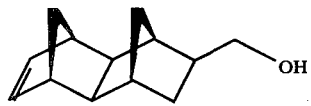

FIG. 11 is the infra-red spectrum for bulked fractions 3-11 of the distillation product of the reaction product of Example IV containing the compound having the structure:

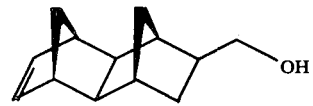

Figure 12:
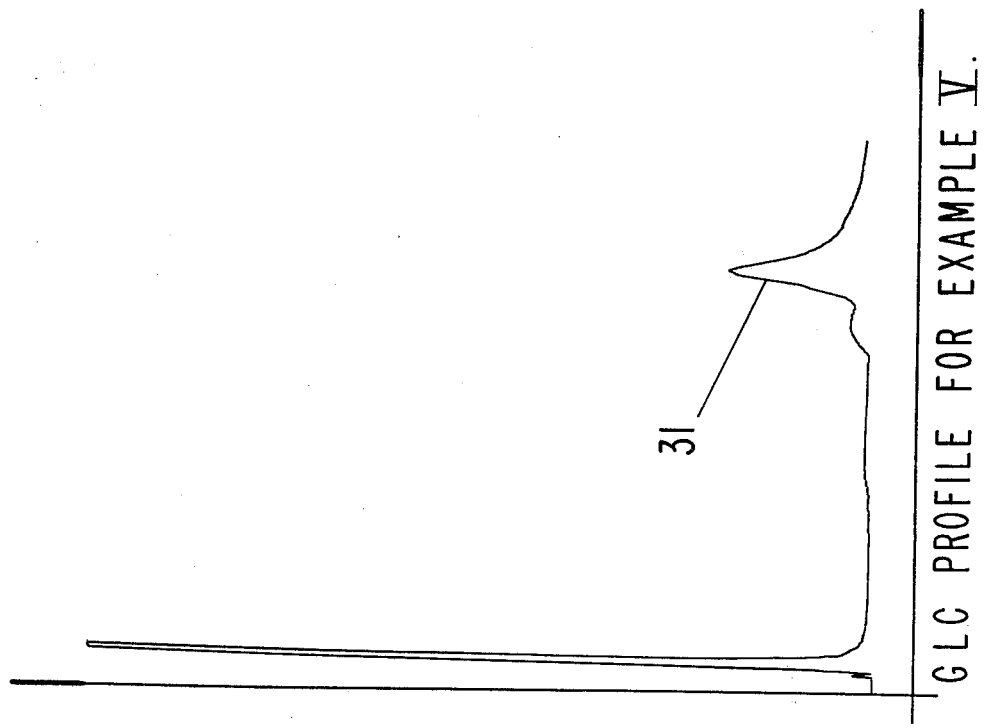

FIG. 12 is the GLC profile for the reaction product of Example V containing the compound having the structure:

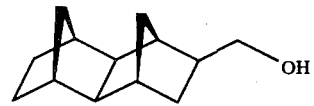

FIG. 13 is the NMR spectrum for fraction 8 of the distillation product of the reaction product of Example V containing the compound having the structure:

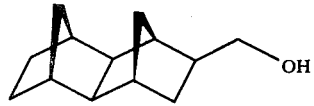

FIG. 14 is the infra-red spectrum for fraction 8 of the distillation product of the reaction product of Example V containing the compound having the structure:

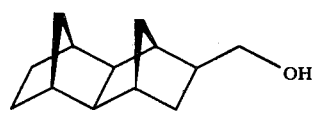

Figure 15:
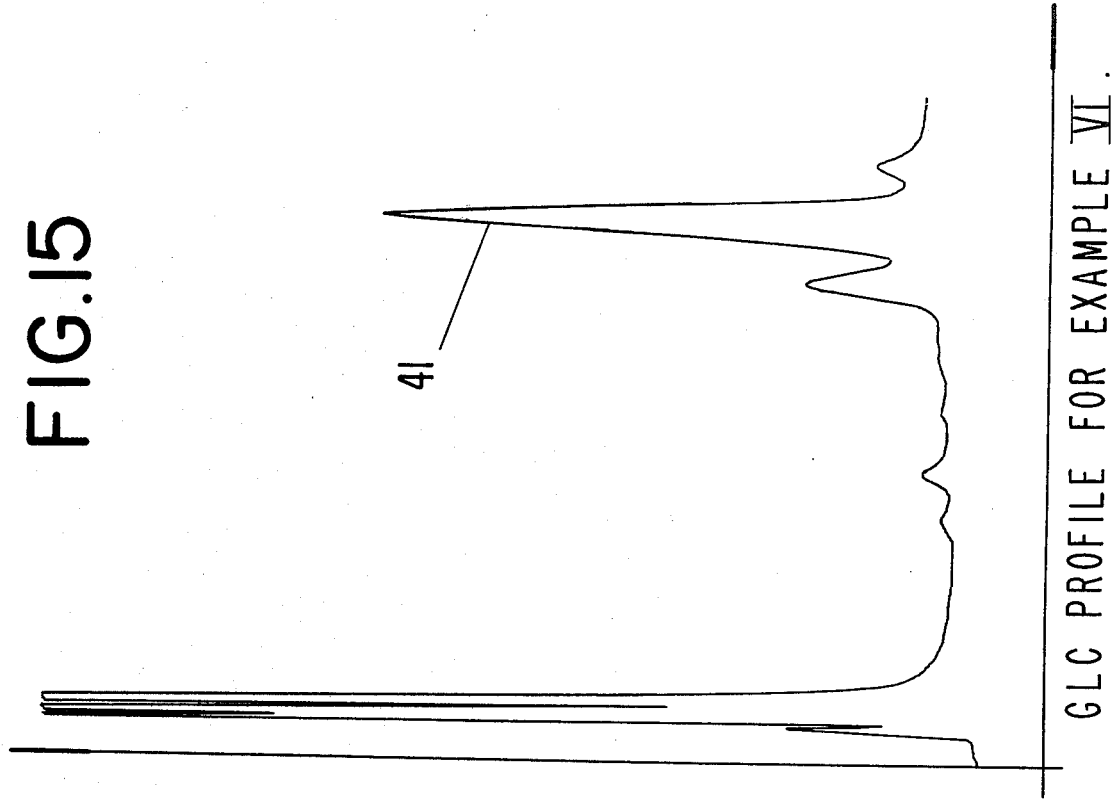

FIG. 15 is the GLC profile for the reaction product of Example VI containing the compound having the structure:

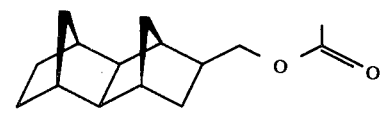

FIG. 16 is the NMR spectrum for fraction 6 of the distillation product of the reaction product of Example VI containing the compound having the structure:

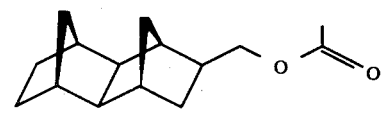

FIG. 17 is the infra-red spectrum for fraction 6 of the distillation product of the reaction product of Example VI containing the compound having the structure:

Figure 18:
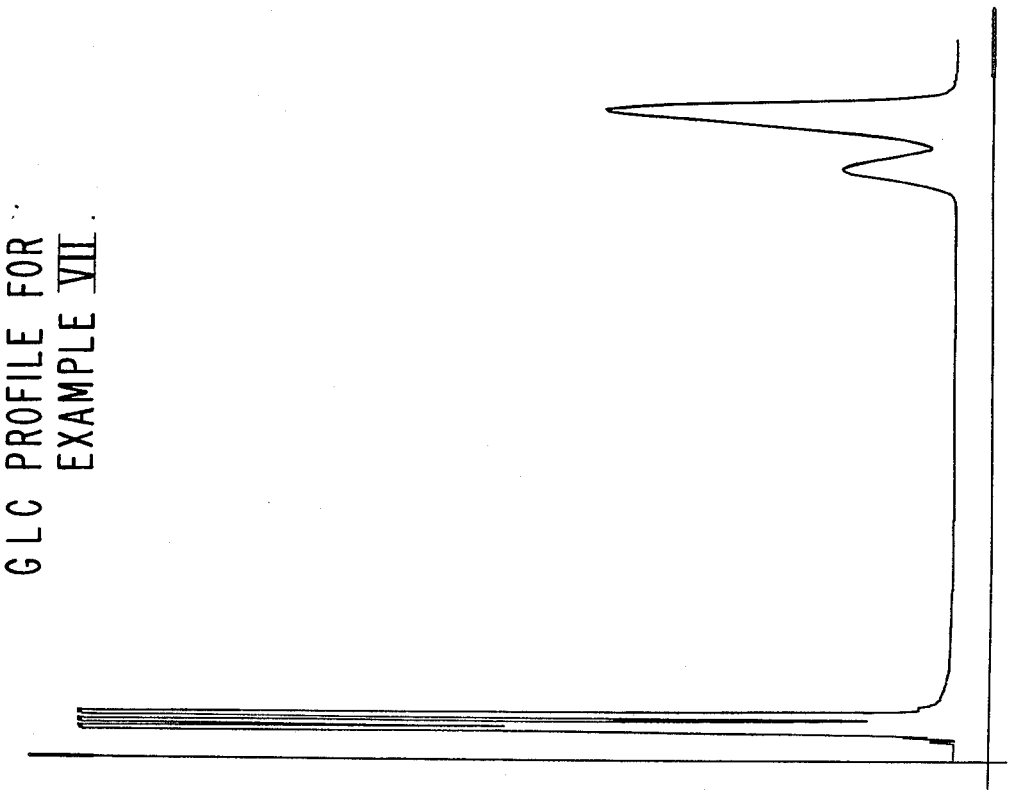

FIG. 18 is the GLC profile for the reaction product of Example VII containing the compound having the structure:

Figure 19:
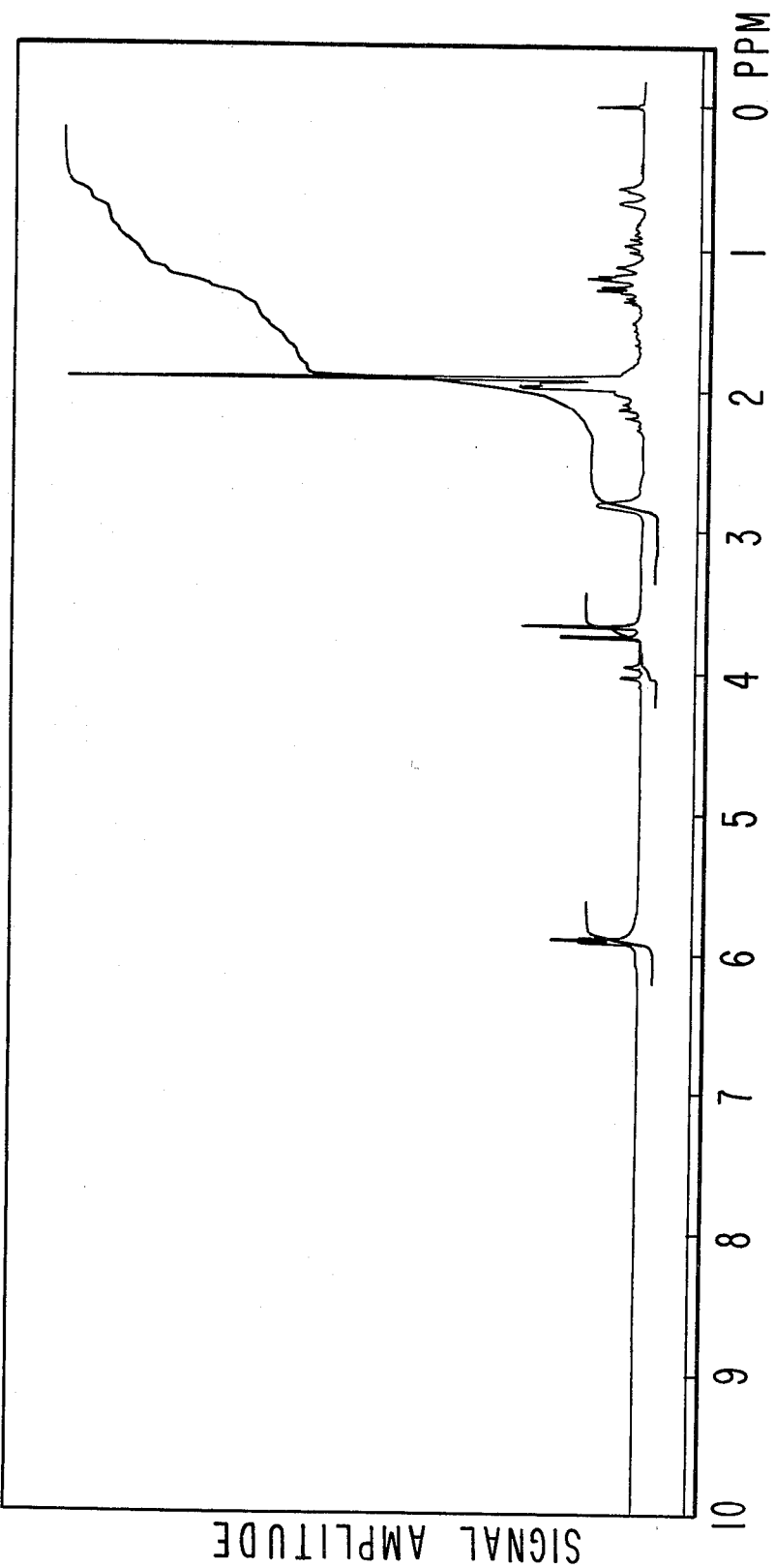

FIG. 19 is the NMR spectrum for fraction 9 of the distillation product of the reaction product of Example VII containing the compound having the structure:

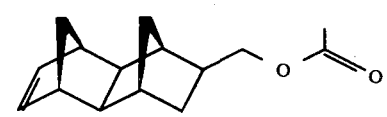

Figure 20:
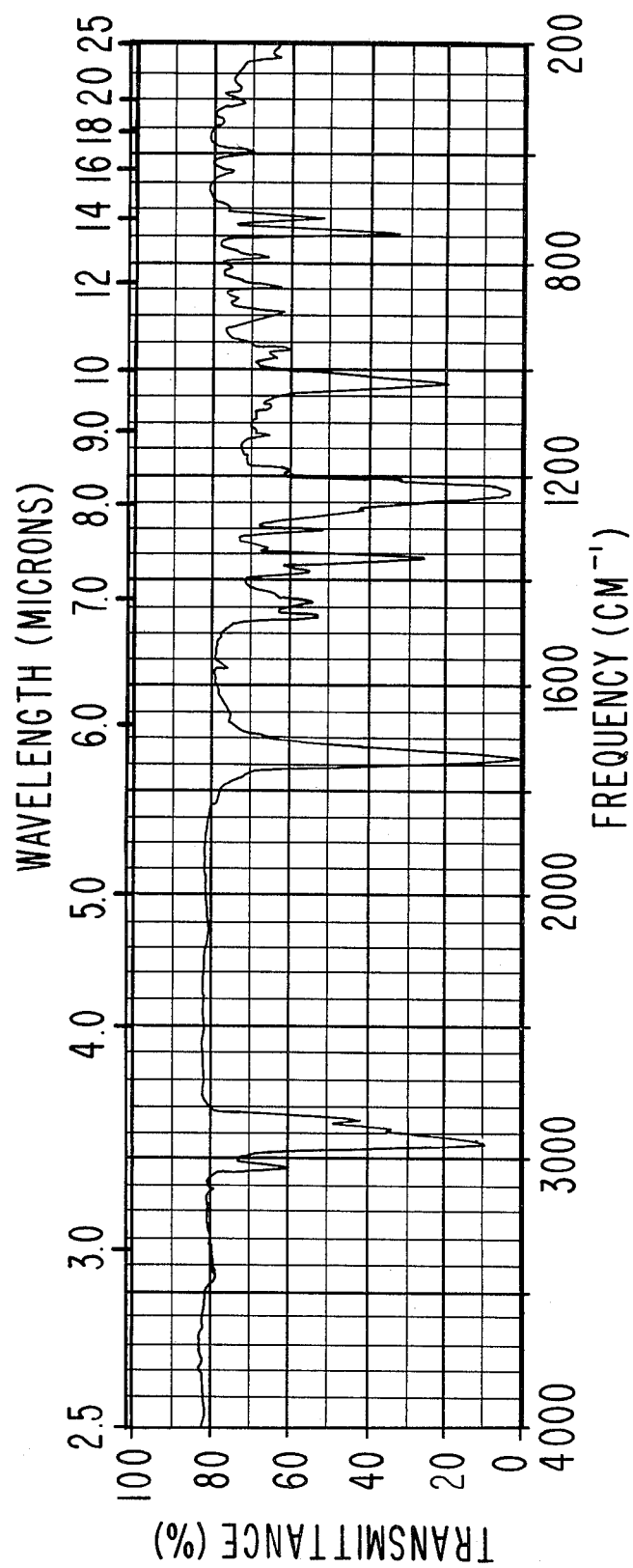

FIG. 20 is the infra-red spectrum for fraction 9 of the distillation product of the reaction product of Example VII containing the compound having the structure:

Figure 21:
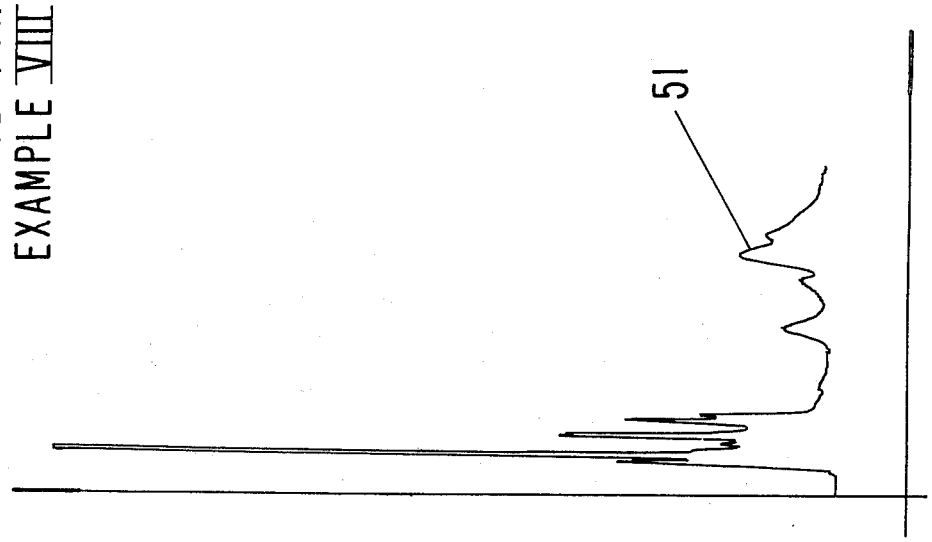

FIG. 21 is the GLC profile for the reaction product of Example VIII containing a mixture of compounds defined according to the structures:

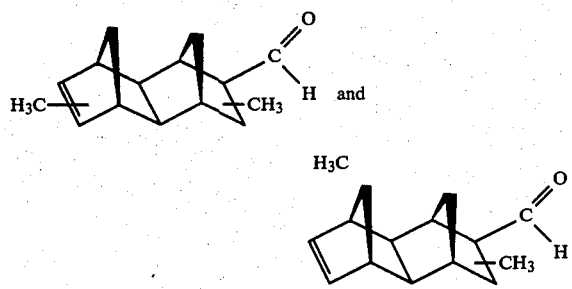

Figure 22:
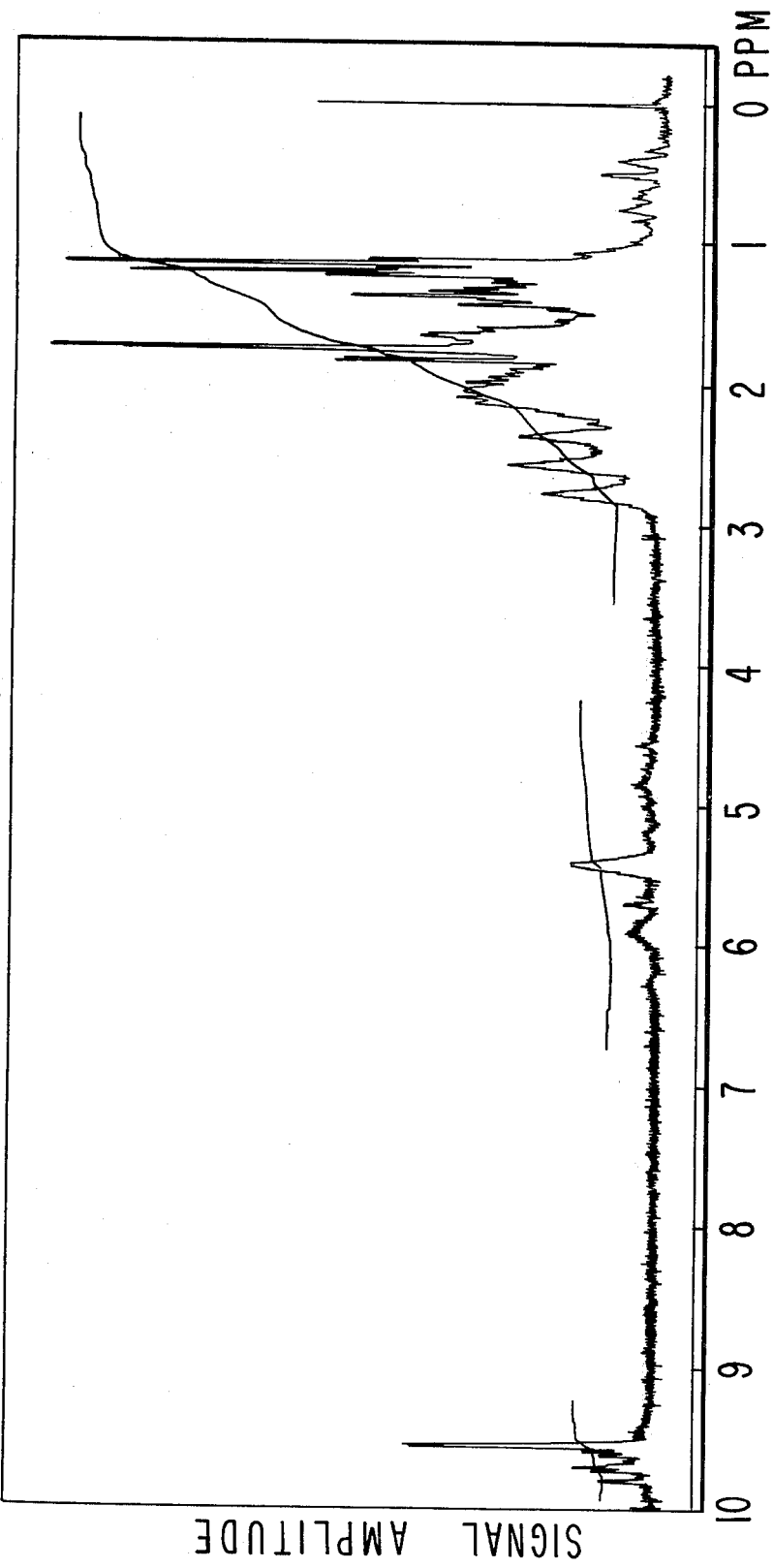

FIG. 22 is the NMR spectrum for Peak 51 of the GLC profile of FIG. 21 for the mixture of compounds defined according to the structures:

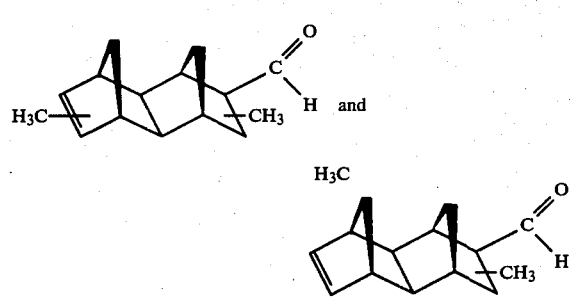

Figure 23:
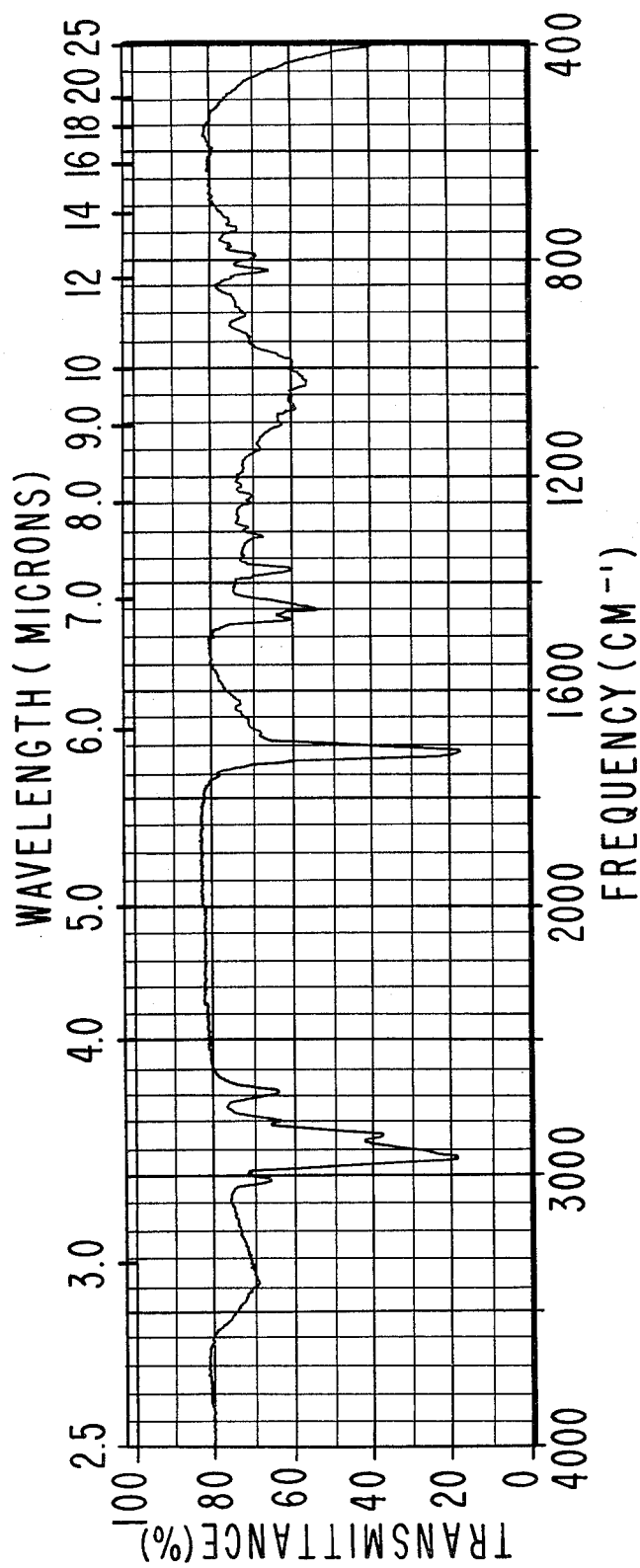

FIG. 23 is the infra-red spectrum for Peak 51 of the GLC profile of FIG. 21 for the reaction product of Example VIII containing a mixture of compounds defined according to the structures:

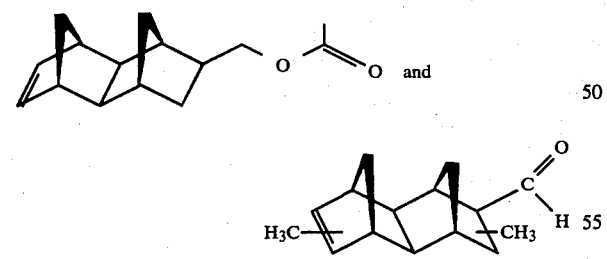

Figure 24:
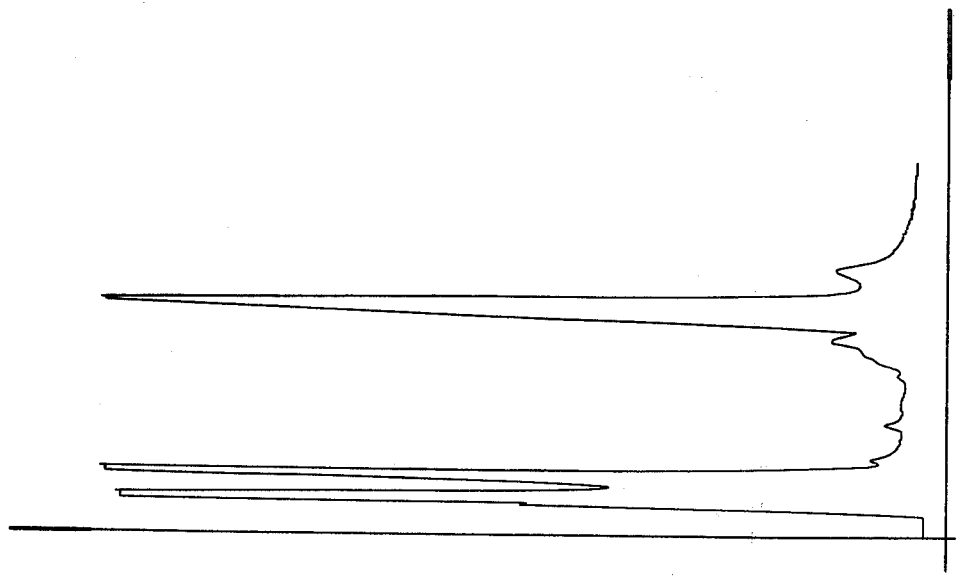

FIG. 24 is the GLC profile for the reaction product of Example IX containing the compound defined according to the structure:

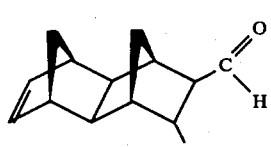

Figure 25:
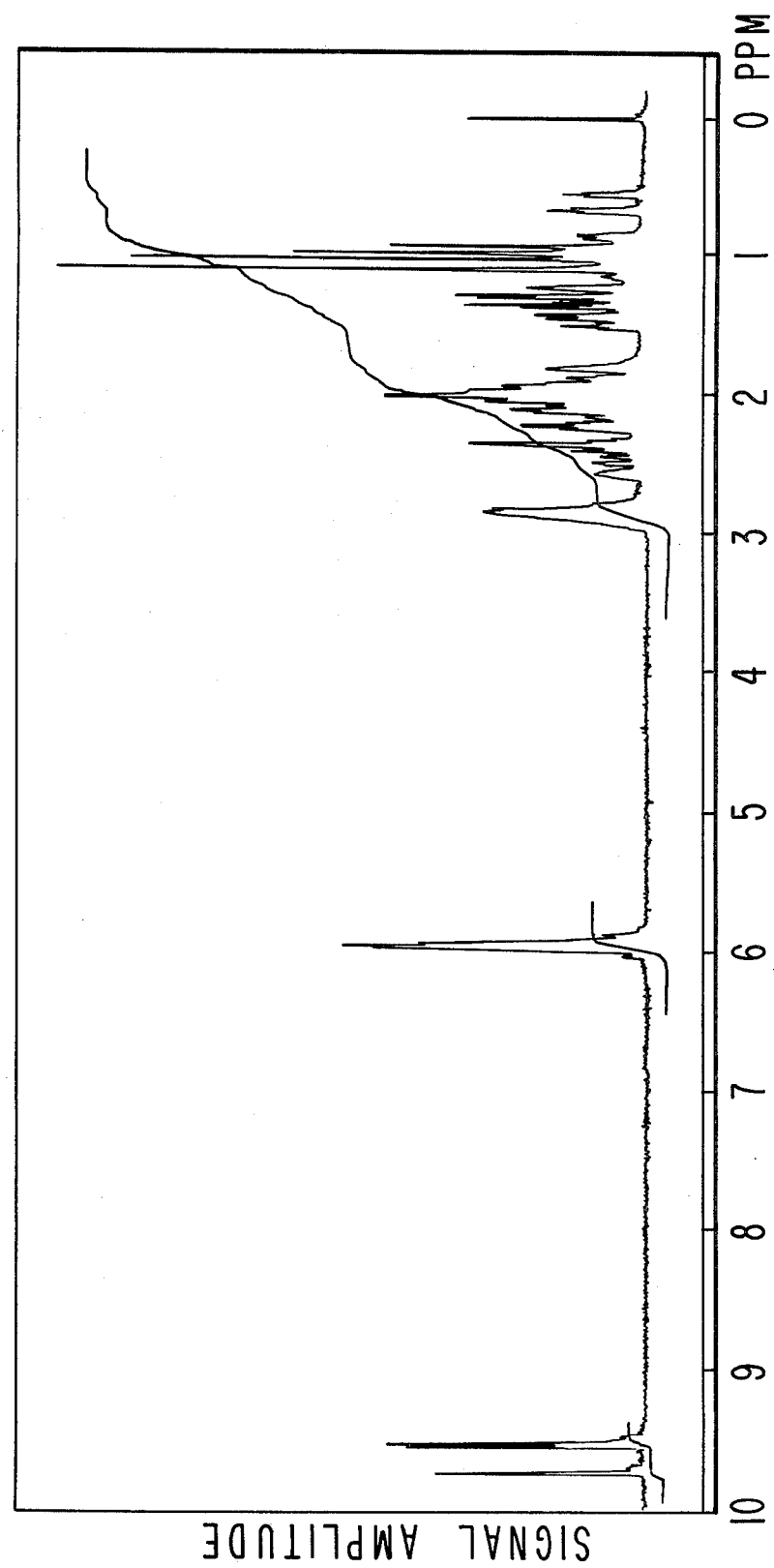

FIG. 25 is the NMR spectrum for the distillation product of the reaction product of Example IX containing the compound having the structure:

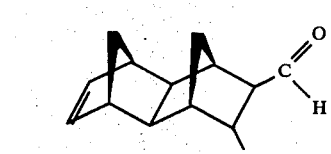

Figure 26:
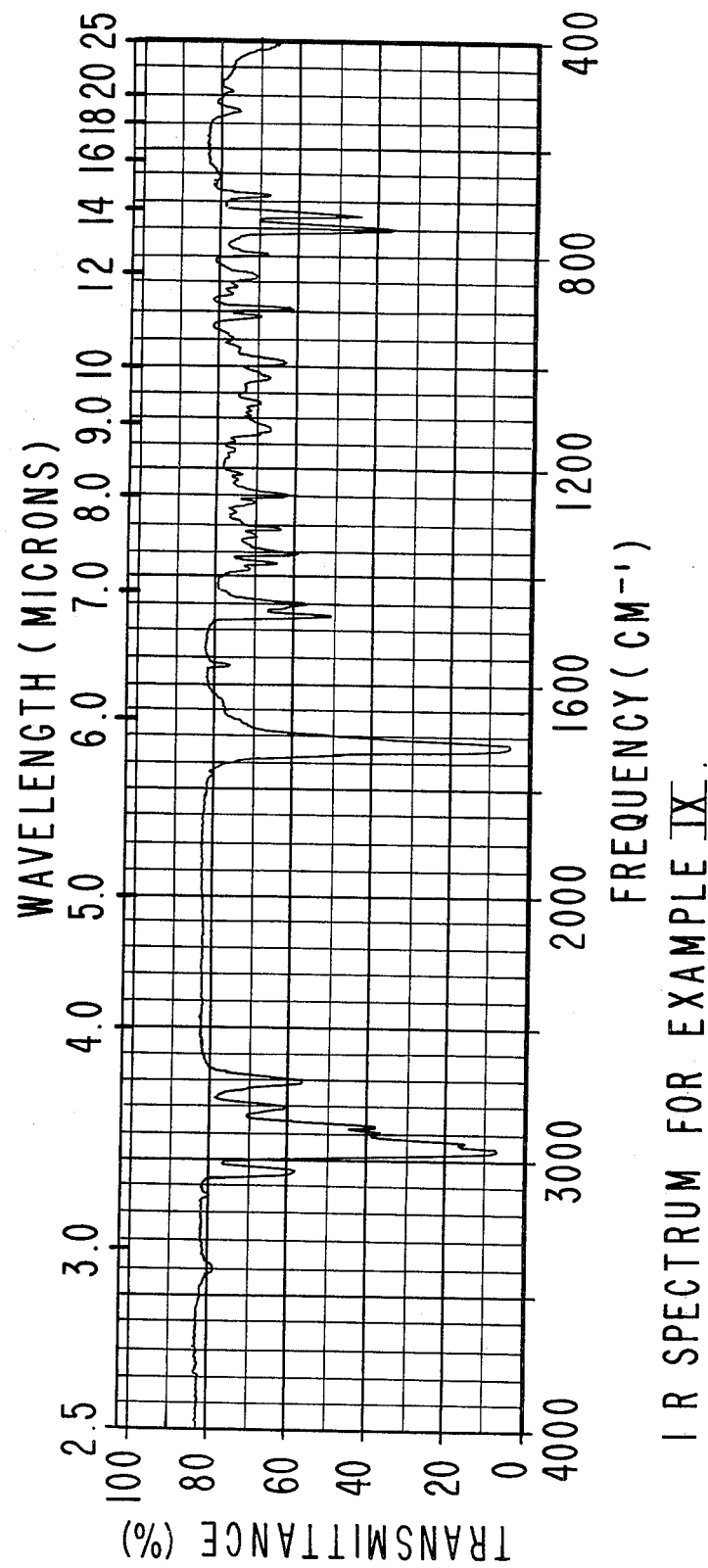

FIG. 26 is the infra-red spectrum for the distillation product of the reaction product of Example IX containing the compound having the structure:

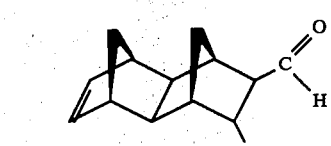

Figure 27:
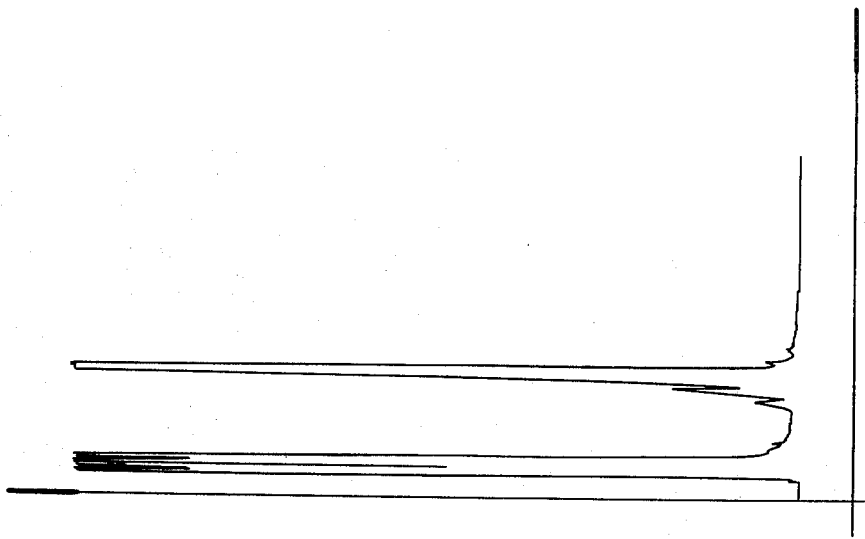

FIG. 27 is the GLC profile for the reaction product of Example X containing the compound having the structure:

FIG. 28 is the NMR spectrum for the distillation product of the reaction product of Example X containing the compound having the structure:

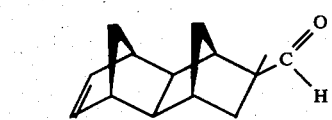

FIG. 29 is the infra-red spectrum for the distillation product of the reaction product of Example X containing the compound having the structure:

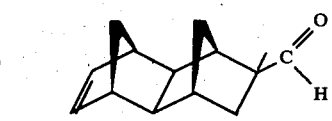

DETAILED DESCRIPTION OF THE DRAWINGS

Figure 1:
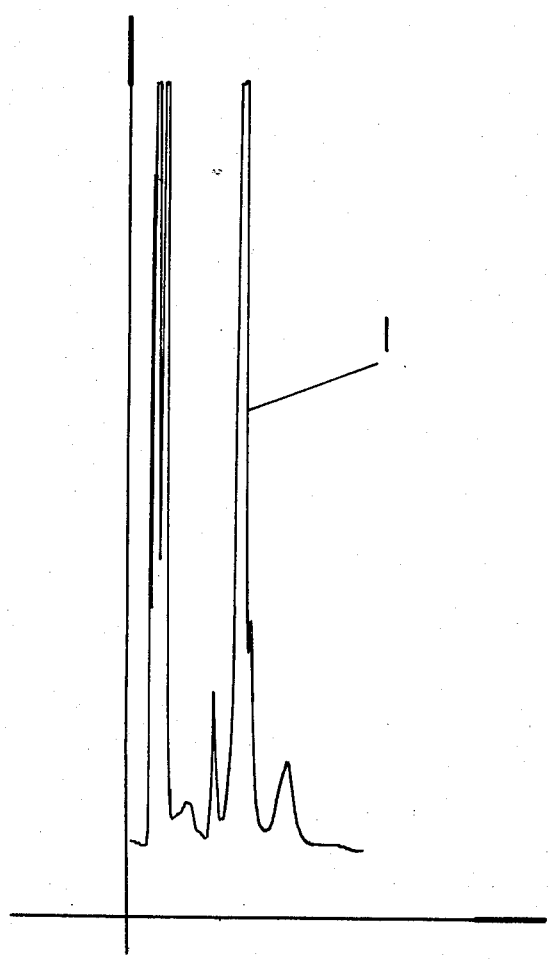
FIG. 1 is the GLC profile for the reaction product of Example I containing the compound having the structure.

FIG. 1 is the GLC profile for the reaction product of Example I containing the compound having the structure:

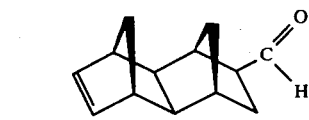

The peak indicated by the reference numeral 1 is the peak for the compound having the structure:

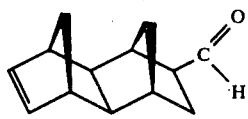

FIG. 7 is the GLC profile for reaction product of Example III. The peak indicated by the reference numeral 11 is for the compound defined according to the structure:

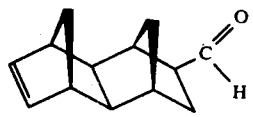

The peak indicated by the reference numeral 12 is for the compound defined according to the structure:

The peak indicated by the reference numeral 13 is for the reaction product defined according to the structure:

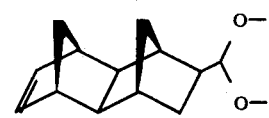

FIG. 9 is the GLC profile for the reaction product of Example IV, bulked distillation fractions 3–11. The peak indicated by the reference numeral 21 is for the reaction product having the structure:

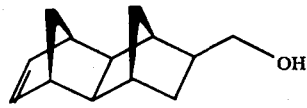

FIG. 12 is the GLC profile for the reaction product of Example V. The peak indicated by the reference numeral 31 is for the reaction product having the structure:

FIG. 15 is the GLC profile for the reaction product of Example VI. The peak indicated by the reference numeral 41 is for the reaction product having the structure:

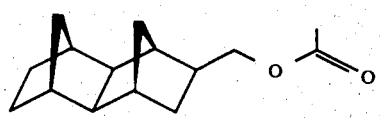

FIG. 21 is the GLC profile for the reaction product of Example VIII. The peak indicated by the reference numeral 51 is for the reaction product which is a mixture of compounds defined according to the structures:

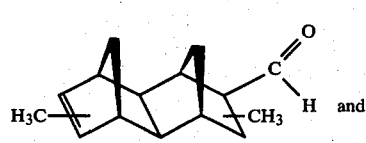

THE INVENTION

It has now been determined that certain mono-oxomethyl substituted polyhydrodimethanonaphthalene derivatives are capable of imparting a variety of flavors and fragrances to various consumable materials.

Briefly, our invention contemplates augmenting or enhancing the flavors and/or fragrances of such consumable materials by adding thereto a small but effective amount of at least one such mono-oxomethyl substituted polyhydrodimethanonaphthalene derivative defined according to the generic structure:

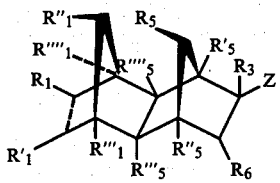

wherein the dashed line represents a carbon-carbon single bond or a carbon-carbon double bond; wherein $R_1$, $R_1'$, $R_1''$, $R_1'''$, $R_1''''$, $R_3$, $R_5$, $R_5'$, $R_5''$, $R_5'''$, $R_5''''$ and $R_6$ represent hydrogen or methyl with the provisos:

(i) at least four of $R_1$, $R_1'$, $R_1''$, $R_1'''$ and $R_1''''$ are hydrogen and (ii) at least four of $R_5$, $R_5'$, $R_5''$, $R_5'''$ and $R_5''''$ represent hydrogen;

and wherein Z represents one of the moieties:

(i) carboxaldehyde having the structure:

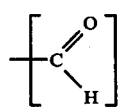

(ii) alkylene dioxy or dialkoxy methyl having the structure:

(iii) hydroxymethyl having the structure:

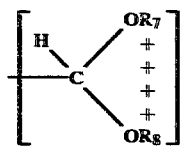

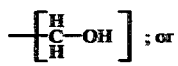 ; or (iv) acetoxymethyl having the structure:

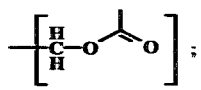 ;

and wherein $R_7$ and $R_8$ taken separately represent $C_1-C_4$ lower alkyl or $R_7$ and $R_8$ taken together represent $C_2-C_4$ alkylene; wherein the line represented by:
[++++]

is either a carbon-carbon single bond when $R_7$ and $R_8$ taken together are $C_2-C_4$ alkylene or no bond at all when $R_7$ and $R_8$ taken separately represent $C_1-C_4$ lower alkyl.

Also described are processes for preparing such mono-oxomethyl substituted polyhydrodimethanonaphthalene derivatives, and processes for using the above defined mono-oxomethyl substituted polyhydrodimethanonaphthalene derivatives for their organoleptic properties and compositions containing said mono-oxomethyl substituted polyhydrodimethanonaphthalene derivatives including perfumes, perfumed articles such as solid or liquid anionic, cationic, nonionic or zwitterionic detergents, perfumed polymers, fabric softeners and cosmetic powders; and foodstuffs, chewing gums, toothpastes, medicinal products, chewing tobaccos, smoking tobaccos and smoking tobacco articles; and flavoring compositions (e.g., for foodstuffs, chewing gums, chewing tobaccos, medicinal products, toothpastes and smoking tobaccos) and fragrance compositions (e.g., for perfume compositions and compositions for augmenting or enhancing the aroma of perfumed articles such as solid or liquid anionic, cationic, nonionic or zwitterionic detergents or fabric softeners or fabric softener articles or cosmetic powders or perfumed polymers) containing such mono-oxomethyl substituted polyhydrodimethanonaphthalene derivatives.

The mono-oxomethyl substituted polyhydrodimethanonaphthalene derivatives produced according to the processes of our invention which are used in practicing that part of our invention concerning flavoring and fragrance compositions are actually racemic mixtures rather than individual optical isomers such as is the case concerning isomers of patchouli alcohol which are obtained from patchouli oil.

The mono-oxomethyl substituted polyhydrodimethanonaphthalene derivatives of our invention insofar as their fragrance profiles are concerned have intense and long lasting melony, cucumber, violet-like, green, leafy, herbaceous, wormwood-like, floral, cinnamic, sandalwood-like, patchouli-like, vetiver-like, sweaty, animalic and spicy aromas. Insofar as their flavor uses are concerned (e.g., foodstuffs, chewing gums, medicinal products, chewing tobaccos and toothpastes) the mono-oxomethyl substituted polyhydrodimethanonaphthalene derivatives of our invention have sweet, aldehydic, floral, melony, herbaceous, green and artichoke-like aroma and taste profiles.

Insofar as smoking tobacco flavors are concerned the mono-oxomethyl substituted polyhydrodimethanonaphthalene derivatives of our invention have sweet, floral and green aroma profiles prior to smoking and sweet, floral and aramatic aroma and taste nuances on smoking both in the main stream and in the side stream.

The following table sets forth the structure and organoleptic property profiles for specific compounds according to the examples listed herein and located infra:

TABLE I

| Structure of Compound | Fragrance Profile | Food Flavor Profile | Tobacco Flavor Profile |
|---|---|---|---|
|  Produced according to Example I. | A melony, cucumber-like, violet-like, green, herbaceous, wormwood-like, and floral aroma. | Sweet, aldehydic, floral, melony and herbaceous aroma at 0.0001 ppm. | A sweet, floral, herbaceous aroma prior to smoking and a sweet, floral and aramatic flavor and taste on smoking in both the main stream and the side stream. |
| 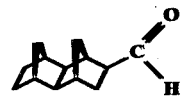 Produced according to Example II. | A floral, fruity (melony) cinnamic aroma. | A sweet, melony, cinnamon-like aroma and taste profile. | A cinnamon/floral aroma prior to smoking and intense cinnamon-like nuances and aramatic tobacco notes on smoking in both the main stream and the side stream. |

TABLE I-continued

| Structure of Compound | Fragrance Profile | Food Flavor Profile | Tobacco Flavor Profile |
|---|---|---|---|
| (structure with OH) Produced according to Example IV. | A sandalwood-like-patchouli-like and vetiver-like aroma profile. | A walnut-like aroma and taste profile. | A nutty/tobacco nuances prior to smoking and woody aroma and taste nuances on smoking in the main stream and the side stream. |
| (structure with O-acetate) Produced according to Example VI. | A floral, fruit (pineapple) aroma profile. | An intense pineapple aroma and taste profile. | A sweet, floral, fruity aroma and taste prior to smoking and fruity virginia-like tobacco notes on smoking in both the main stream and the side stream. |
| (structure with O-acetate) Produced according to Example VII. | A sweaty, musk-like aroma profile. | A green, artichoke-like aroma and taste profile. | — |
| (structures with CHO and CH3) Produced according to Example VIII, infra. | An animalic, leafy, green, herbaceous, floral and violet-like aroma profile with cinnamic and cucumber-like undertones. | A green, melony, minty, herbaceous and floral aroma and taste profile at 2 ppm. | A minty tobacco nuance prior to smoking and minty cooling-like notes on smoking in both the main stream and the side stream. |
| (structure with CHO) Produced according to Example X. | A spicy cinnamic-like aroma. | A spicy, cinnamon-like aroma and taste profile. | A spicy, cinnamon-like aroma and taste profile prior to smoking and spicy turkish oriental-like tobacco nuances on smoking in the main stream and the side stream. |

The mono-oxomethyl substituted polyhydrodimethanonaphthalene derivatives produced according to the process of our invention which are used in practicing that part of our invention concerning flavor and fragrance compositions may be mixtures of isomers or they may be substantially pure forms of exo or endo isomers or specific stereoisomers such as in the case concerning isomers of patchouli alcohol which are obtained from patchouli oil.

The mono-oxomethyl substituted polyhydrodimethanonaphthalene derivatives prepared according to our invention can be obtained by reacting bicyclopentadiene or dimethyl bicyclopentadiene having the structures:

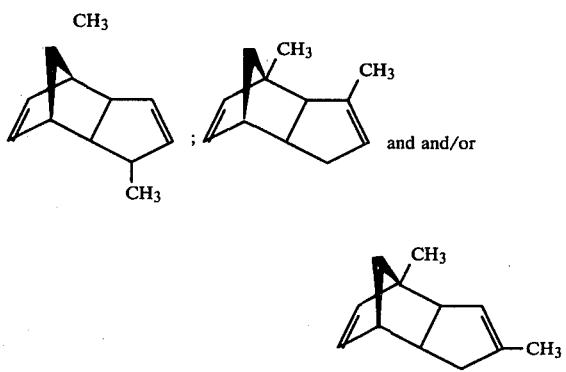

with an acrolein derivative according to the reaction:

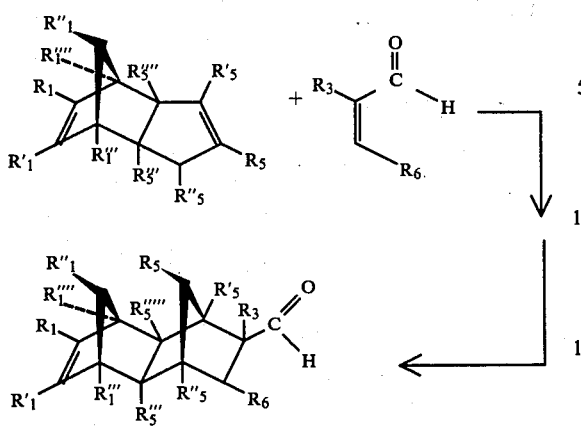

wherein $R_1$, $R_1'$, $R_1''$, $R_1'''$, $R_1''''$, $R_3$, $R_5$, $R_5'$, $R_5''$, $R_5'''$, and $R_5''''$ are defined, supra. The reaction is carried out at pressures in the range of from about 150 psig up to about 500 psig and at temperatures in the range of from about 150° C. up to about 250° C. in the presence of or in the absence of an inert solvent. When the solvent is used it is preferred to use a solvent such as toluene or xylene which can easily be separated from the reaction mass after the completion of the reaction. The ratio of bicyclopentadiene derivative:acrolein derivative may vary from about 0.5:1 up to about 1:0.5 with the preferred mole ratio being about 1:1. The concentration of reactant in the reaction mass may vary from about 100 grams per liter up to about 500 grams per liter. At the end of the reaction the pressure vessel is opened and the contents are distilled preferably by means of fractional distillation. The reaction product can be used "as is" for its organoleptic properties or it may be further reacted as set forth, infra.

The mechanism for this reaction is as follows:

(I)

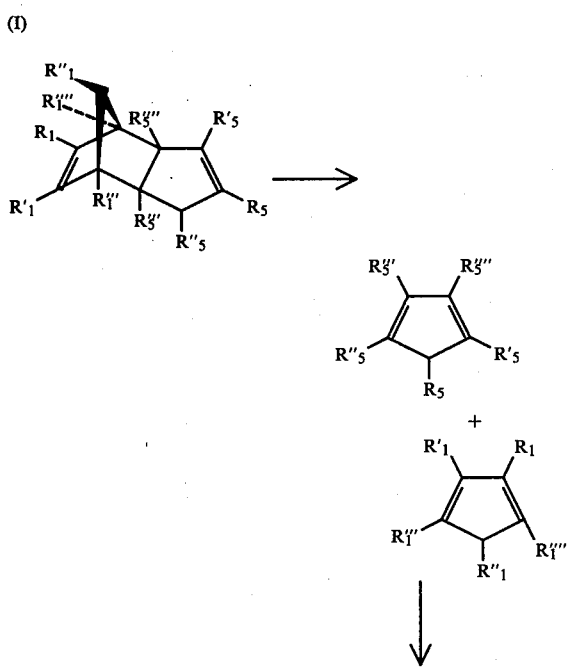

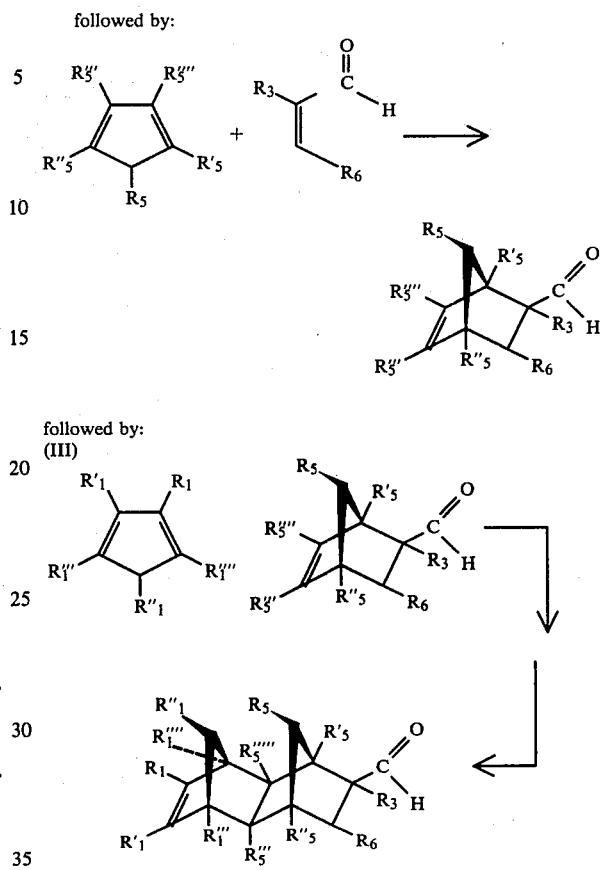

wherein $R_1$, $R_1'$, $R_1''$, $R_1'''$, and $R_1''''$ and $R_3$, $R_5$, $R_5'$, $R_5''$ $R_5'''$, $R_5''''$ and $R_6$ are defined, supra.

The resulting aldehyde defined according to the structure:

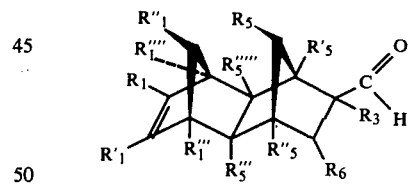

may then be reduced to form the corresponding saturated polycyclic carboxaldehydes or unsaturated polycyclic carboxaldehydes or saturated polycyclic carbinols or unsaturated polycyclic carbinols or the resulting aldehyde may be then reacted with an alkanol or alkanediol to form polycyclic carbinyl acetals, or cyclic acetals. In turn, the resulting carbinols may be acylated as with acetic anhydride or acetyl chloride or acetyl bromide to form the corresponding saturated polycyclic carbinol acetates or unsaturated polycyclic carbinol acetates.

Thus, when reacting the aldehyde derivative defined according to the genus having the structure:

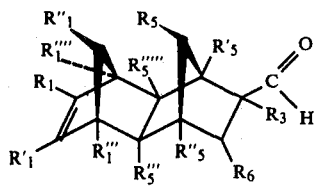

with one mole of hydrogen per mole of aldehyde at a pressure in the range of from about 50 psig up to about 200 psig and in the presence of a catalyst such as palladium supported on carbon, palladium supported on barium sulfate, palladium supported on calcium sulfate or palladium supported on calcium carbonate (for example: 5% palladium supported on calcium sulfate, 5% palladium supported on calcium carbonate or 10% palladium on carbon) at a temperature in the range of from about 10° C. up to 140° C., the aldehyde will be reduced to the saturated polycyclic carboxaldehyde according to the reaction:

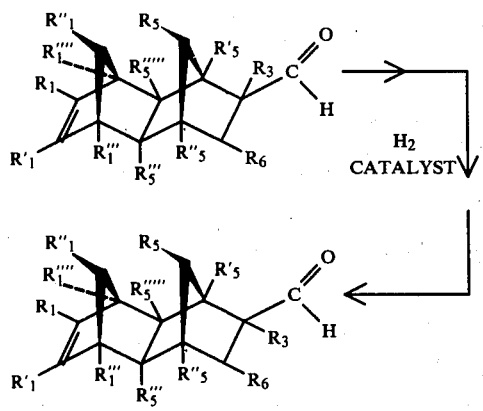

On the other hand when two moles of hydrogen are used per mole of aldehyde, the reduction is such that a saturated polycyclic carbinol is formed according to the reaction:

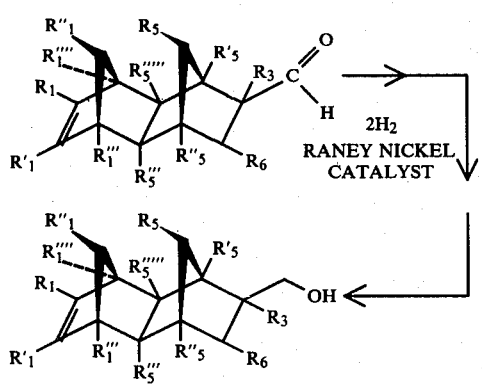

The aldehyde genus defined according to the structure:

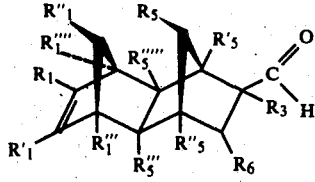

may be reduced with an alkali metal borohydride or lithium aluminum hydride in the presence of an inert solvent to form the unsaturated polycyclic carbinol according to the reaction:

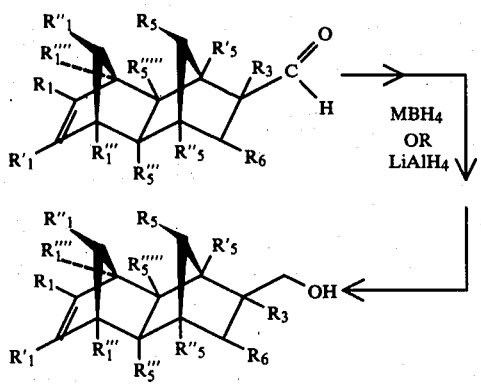

wherein M represents alkali metal such as lithium, sodium or potassium.

The reaction is carried out in the presence of an inert solvent such as isopropyl alcohol, n-propyl alcohol, ethyl alcohol or methyl alcohol or diethyl ether or tetrahydrofuran. The reaction is carried out at a temperature in the range of from about 20° C. up to reflux conditions (depending upon the solvent used) and is most conveniently and preferably carried out at atmospheric pressures since higher pressures do not give rise to higher yields or higher conversions. The mole ratio of alkali metal borohydride:aldehyde reactant or lithium aluminum hydride:aldehyde reactant may vary from about 0.2:1 up to about 1:1 with a preferred mole ratio of 0.25:1 up to 0.5:1.

Both the saturated and unsaturated polycyclic carbinols defined according to the structures:

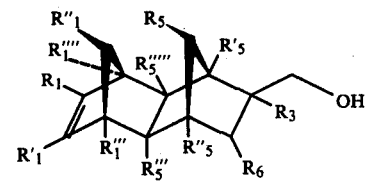

and

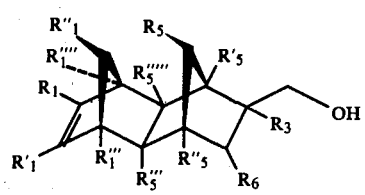

may be further reacted as by acetylation using acetic anhydride or acetyl chloride. The reaction with acetic anhydride is preferably carried out in the presence of an inert solvent at reflux conditions at atmospheric pressure. Such an inert solvent is toluene or xylene, the solvents being inert and having boiling points such that the reaction may proceed efficiently and in a minimum amount of time. Preferably the mole ratio of acetic anhydride:carbinol reactant is from about 0.5:1.5 up to about 1.5:0.5 with a most preferred ratio of acetic anhydride:carbinol reactant being 1–1.5:1. Each of these reactions is set forth as follows:

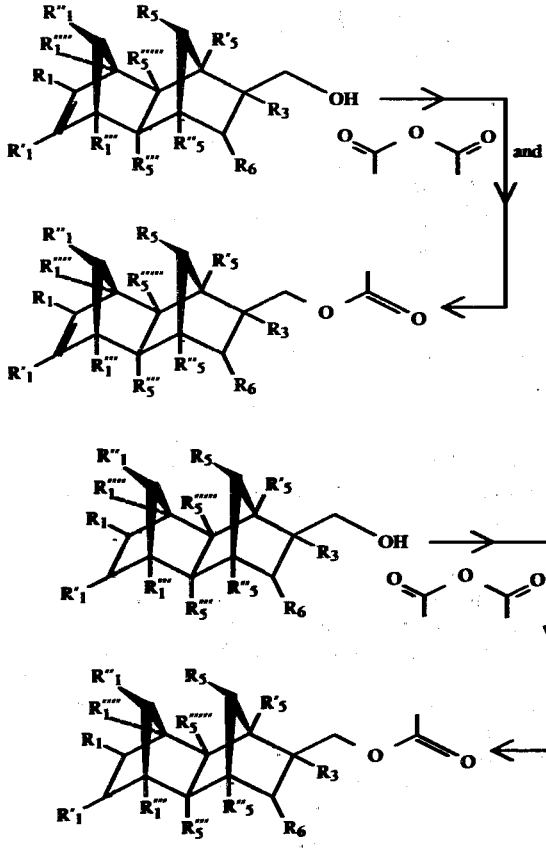

In addition, the aldehyde derivatives defined according to the structure:

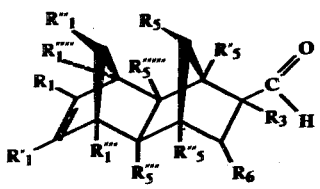

may be converted into cyclic or acyclic acetals by means of reaction of the aldehyde with a $C_1$–$C_4$ alkanol or a $C_2$–$C_4$ alkanediol according to the reaction:

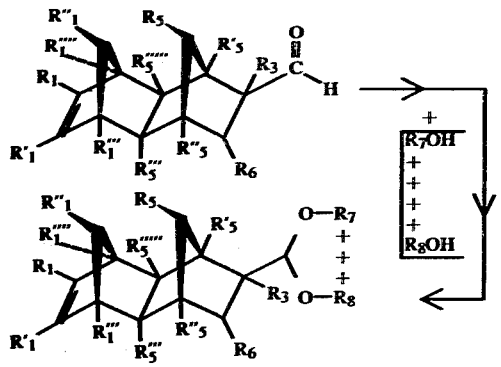

wherein $R_1$, $R_1'$, $R_1''$, $R_1'''$, $R_1''''$, $R_3$, $R_5$, $R_5'$, $R_5''$, $R_5'''$, $R_5''''$, $R_6$, $R_7$, $R_8$ and the line [+ + + +] are defined, supra.

The reaction is carried out in the presence of a protonic acid catalyst or a Lewis acid catalyst at a temperature in the range of from about 30° C. up to about 90° C. Preferred catalysts are boron trifluoride etherate, 20% sulfuric acid, saturated aqueous, ammonium chloride and stannic chloride.

The preferred mole ratio of alkane diol:aldehyde reactant may vary from about 1:1 up to aboue 2:1 and the preferred mole ratio of alkylenediol:aldehyde reactant may vary from about 2:1 up to about 4:1.

At the end of each of the foregoing reactions the reaction product may, if desired, be separated from the resultant reaction mass by fractional distillation or preparative GLC (vapor phase, chromatography). However, if the desired reaction product is to be utilized as a reaction intermediate, the necessity of careful rectification of the reaction product in order to achieve odor acceptable substances or flavor acceptable substances is not usually necessary since the resultant reaction product will be further reacted.

Thus, the individual mono-oxomethyl substituted polyhydrodimethanonapthalene derivatives of our invention can be obtained in pure form or in substantially pure form by conventional purification techniques. The products can be purified and/or isolated not only by distillation (as mentioned, supra), but also using extraction, crystallization, preparative chromatographic techniques and the like. It has been found desirable to purify the mono-oxomethyl substituted polyhydrodimethanonaphthalene derivatives of our invention by fractional distillation in vacuo.

When the mono-oxomethyl substituted polyhydrodimethanonaphthalene derivatives of our invention are used as food flavor adjuvants, the nature of the co-ingredients included with said mono-oxomethyl substituted polyhydrodimethanonaphthalene derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste."

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable, plastic gum base such as chicle, or substitutes therefor, including guttakay rubber or certain comestible natural or synthetic resins or waxes. Incorporated with the gum base in admixture therewith may be plasticizers or softening agents, e.g., glycerine, and a flavoring composition which incorporates one or more of the mono-oxomethyl substituted polyhydrodimethanonaphthalene derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising, broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy-anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nitrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta-beta-dimethylacrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, $\beta$-damascone, $\alpha$-damascone, $\beta$-damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl-furfural, cinnamaldehyde, beta-cyclohomocitral 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpin hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl $\alpha$-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyldiphenyl, methyl naphthalene, myrcene, naphthalene, octadecane, tetradecane, tetramethyl-naphthalene, tridecane, trimethylnaphthalene, undecane, caryophyllene, $\alpha$-phellandrene, $\beta$-phellandrene, p-cymene 1-$\alpha$-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; Δ-decalactone; γ&Δ-undecalactone; γ&Δ-dodecalactone; sulfides, e.g., methyl sulfide and other materials such as maltol, and acetals (e.g., 1,1-diethoxyethane, 1-1-dimethoxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatible with the mono-oxomethyl substituted polyhydrodimethanonaphthalene derivatives of our invention by not covering or spoiling the organoleptic properties (aroma and/or taste thereof); (ii) be non-reactive with the mono-oxomethyl substituted polyhydrodimethanonaphthalene derivatives of our invention; and (iii) be capable of providing an environment in which the mono-oxomethyl substituted polyhydrodimethanonaphthalene derivatives of our invention can be dispersed or admixed to provide a homogeneous medium In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of mono-oxomethyl substituted polyhydrodimethanonaphthalene derivative(s) of our invention employed in a particular instance can vary over a relatively wide range, depending upon the desired organoleptic effects to be achieved. Thus, correspondingly greater amounts would be necessary in those instances wherein the ultimate food composition to be flavored (e.g., with a peppermint flavor, or a specific vegetable flavor such as an artichoke flavor) is relatively bland to the taste, whereas relatively minor quantities may suffice for purposes of enhancing a composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, of flavoring composition.

The use of insufficient quantities of mono-oxomethyl substituted polyhydrodimethanonaphthalene derivatives of our invention will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of mono-oxomethyl substituted polyhydrodimethanonaphthalene derivatives of our invention ranging from a small but effective amount, e.g., 0.00001 parts per million up to about 100 parts per million based on total composition, are suitable. Concentrations in excess of the maximum quantity stated are not normally recommended since they fail to provide commensurate enhancement of organoleptic properties. In those instances wherein the mono-oxomethyl substituted polyhydrodimethanonaphthalene derivatives of our invention are added to the foodstuff as an integral component of a flavoring composition, it is of course essential that the total quantity of flavoring composition employed be sufficient to yield an effective mono-oxomethyl substituted polyhydrodimethanonaphthalene derivative concentration in the foodstuff product.

Food flavoring compositions prepared in accordance with the present invention preferably contain the mono-oxomethyl substituted polyhydrodimethanonaphthalene derivatives of our invention in concentrations ranging from about 0.01% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the mono-oxomethyl substituted polyhydrodimethanonaphthalene derivatives of our invention with, for example, gum arabic, gum tragacanth, carrageenan, xanthangum, guargum, mixtures of same and the like, and thereafter spray-drying the resultant mixture whereby to obtain the particular solid product. Prepared flavor mixes in powder form, e.g., a fruit flavored powder mix, are obtained by mixing the dried solid components, e.g., starch, sugar and the like, and one or more mono-oxomethyl substituted polyhydrodimethanonaphthalene derivatives of our invention in a dry blender until the requisite degree of uniformity is achieved.

It is presently preferred to combine with the mono-oxomethyl substituted polyhydrodimethanonaphthalene derivatives of our invention, the following adjuvants:
Oil of Cubeb;
α-phellandrene;
β-phellandrene;
Oil of Coriander;
Oil of Pimento Leaf;
Oil of Patchouli;
Alpha Pinene;
Beta Pinene;
Beta-caryophyllene;
Dihydrocarveol;
Piperonal;
Piperine;
Chavicine;
Piperidine;
Oil of Black Pepper;
Black Pepper Oleoresin;
Capsicum;
Oil of Nutmeg.
Cardamom Oil;
Clove Oil;

Spearmint Oil;
Oil of Peppermint;
Ethyl-2-methyl butyrate;
Vanillin;
Butyl valerate;
2,3-Diethyl pyrazine;
Methyl cyclopentenolone;
Benzaldehyde;
Valerian Oil Indian;
Propylene glycol;
Acetaldehyde;
Isobutyraldehyde;
Isovaleraldehyde;
Dimethyl sulfide;
Isobutyl acetate;
Isoamyl acetate;
Phenylethyl acetate;
Diacetyl;
Acetophenone;
Furfural
Phenylacetaldehyde
Isoamyl alcohol;
β-Phenylethyl alcohol;
α-Phenyl ethyl alcohol
γ-Butyrolactone;
y-Butyrolactone;
3-Phenyl-4-pentenal;
3-Phenyl-3-pentenal;
3-Phenyl-2-pentenal;
2-Methyl pyrazine;
2,6-Dimethyl pyrazine;
2,3,5,6-Tetramethyl pyrazine;
2,3,5-Trimethylpyrazine;
2-Ethyl-3-methylpyrazine;
2-Ethyl-3,5-dimethylpyrazine;
2-Ethyl-3,6-dimethylpyrazine;
2-Ethyl-5-methylpyrazine;
2(n-pentyl) thiazole;
2(i-butyl) thiazole;
2(i-propyl) thiazole;
2(n-propyl) thiazole;
2-phenyl-4-pentenal;
2-phenyl-4-pentenaldimethylacetal;
Methional;
4-methylthiobutanal;
2-ethyl-3-acetylpyrazine
trans-2-hexenal;
Hydrolyzed vegetable protein;
Monosodium glutamate;
Celery Oil;
Lemon Oil:
Mustard Oil;
2,4-dimethyl-$\Delta^3$-thiazoline;
4,5-dimethyl-$\Delta^3$-thiazoline;
2,4,5-trimethyl-$\Delta^3$-thiazoline;
2-propyl-2,4,5-trimethyl-$\Delta^3$-thiazoline;
2-ethyl-2,4,5-trimethyl-$\Delta^3$-thiazoline;
2-(2'butyl)-4-methyl-$\Delta^3$-thiazoline;
2-n-butyl-4,5-dimethyl-$\Delta^3$ thiazoline;
2-benzeyl-4-methyl-$\Delta^3$-thiazoline;
2,5-dimethyl-2-benzyl-$\Delta^3$-thiazoline;
2-(2'-methyl-n-propyl)-4.5-dimethyl-$\Delta^3$ thiazoline;
β-Damascone
β-Damascenone; and
trans,trans$\Delta^3$-Damascone The mono-oxomethyl substituted polyhydrodimethanonaphthalene derivatives of our invention can be used to contribute melony, cucumber, violet-like, green, leafy, herbaceous, wormwood-like, floral, cinnamic, sandalwood-like, patchouli-like, vetiver-like, sweaty, animalic and spicy aroma nuances to perfume compositions, perfumed articles (such as solid or liquid anionic, cationic, nonionic or zwitterionic detergents, fabric softeners, fabric softener articles and perfumed polymers) and colognes. As olfactory agents the mono-oxomethyl substituted polyhydrodimethanonaphthalene derivatives of our invention can be formulated into or used as components of a "perfume composition".

The term "perfume composition" is used herein to mean a mixture of organic compounds including, for example, alcohols (other than the alcohols of our invention), aldehydes (other than the aldehydes of our invention), ketones, nitriles, ethers, lactones, acetals (other than the acetals of our invention), esters (other than the esters of our invention), and frequently hydrocarbons which are admixed so that the combined odors of the individual components produce a pleasant or desired fragrance. Such perfume compositions usually contain: (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions the individual component will contribute its particular olfactory characteristics, but the overall effect of the perfume composition will be the sum of the effects of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of the mono-oxomethyl substituted polyhydrodimethanonaphthalene derivatives of our invention which will be effective in perfume compositions depends on many factors, including the other ingredients, their amounts and the effects which are desired. It has been found that perfume compositions containing as little as 0.2% of one or more of the mono-oxomethyl substituted polyhydrodimethanonaphthalene derivatives of our invention, or even less, can be used to impart melony, cucumber-like, violet-like, green, leafy, herbaceous, wormwood-like, floral, cinnamic, sandalwood-like, patchouli-like, vetiver-like, sweaty, animalic, and spicy aroma nuances to soaps, cosmetics, solid or liquid anionic, cationic, nonionic, or zwitterionic detergents, fabric softeners, fabric softener articles, perfumed polymers, cosmetic powders, hair preparations and other products. The amount employed can range up to 50% or higher and will depend on considerations of cost, nature of the end product, the effect desired on the finished product and a particular fragrance sought.

The mono-oxomethyl substituted polyhydrodimethanonaphthalene derivatives of our invention can be used alone or in a perfume composition as an olfactory component in solid or liquid anionic, cationic, nonionic or zwitterionic detergents, fabric softeners, and soaps; space odorants and deodorants; perfumes; colognes, toilet waters; bath salts; hair preparations such as lacquers, brilliantines, pomades, and shampoos; cosmetic preparations such as creams, deodorants, hand lotions, and sun screens; powders such as talcs, dusting powders, face powder and the like. When used as an olfactory component of a perfumed article, as little as 0.005% of one or more of the mono-oxomethyl substituted polyhydrodimethanonaphthalene derivatives of our invention will suffice to impart an interesting melony, cucumber, violet-like, green, leafy, herbaceous, wormwood-like, floral, cinnamic, sandalwood-like, patchouli-like, vetiver-like, sweaty, animalic and spicy aromas. Generally, no more than 0.8% is required in the perfumed article. Thus, to be specific, the range of mono-oxomethyl substituted polyhydrodimethanonaphthalene derivatives of our invention useful in perfumed articles varies from about 0.005% up to about 0.8%.

In addition, the perfume composition of our invention can contain a vehicle or carrier for the mono-oxomethyl substituted polyhydrodimethanonaphthalene derivatives of our invention. The vehicle can be a liquid such as an alcohol such as ethanol, a glycol such as propylene glycol, or the like. The carrier can be an absorbent solid such as a gum or components for encapsulating the composition by coacervation such as gelatin or for encapsulating the composition by forming polymers around a central liquid core such as a urea formaldehyde capsule.

It is the further object of our invention to provide a smoking tobacco product treated with an additive which will enhance the tobacco aroma, as well as the flavor characteristics of the tobacco product made therefrom. Also, it is an object of the present invention to provide a smoking tobacco product having a material added to the tobacco which will readily transfer to the tobacco smoke and pass through a filter element (even of a high filtration type) so that the natural flavor qualities of the tobacco smoke are enhanced.

Another object of our invention is the provision of smoking tobacco products, such as cigarettes, cigars, pipe tobacco, or tobacco smoke filters, having added thereto a releasable flavor additive which will impart a desirable fresh natural taste to the smoking product when smoked.

Thus, in general, our invention further contemplates providing an organoleptically improved tobacco product having added thereto one or more mono-oxomethyl substituted polyhydrodimethanonaphthalene derivatives of our invention which imparts to the product the enhanced and desirable fresh flavor and aroma of natural tobacco. The mono-oxomethyl substituted polyhydrodimethanonaphthalene derivatives of our invention are individually and in combination readily transferred either from the filter section or the tobacco section into the smoke stream when the tobacco product is smoked. The organoleptic qualities of the mono-oxomethyl substituted polyhydrodimethanonaphthalene derivatives of our invention particularly when transferred to the tobacco smoke, impart desirable fresh, oriental, spicy, floral, citrusy flavor and aroma nuances to tobacco causing the tobacco to be more desirable and causing a change from the "Virginia" and "Burley" types to the "imported", "Turkish" types.

The mono-oxomethyl substituted polyhydrodimethanonaphthalene of our invention employed to improve the organoleptic qualities of a tobacco product have odor characteristics which can be described as floral, spicy, woody, and cinnamon-like as well as citrusy. The amount of mono-oxomethyl substituted polyhydrodimethanonaphthalene derivatives of our invention taken alone or in combination added to a tobacco product may vary greatly; however a sufficient amount should be used to achieve the desired organoleptic properties for the smoking tobacco product when smoked. We have found that the levels of the mono-oxomethyl substituted polyhydrodimethanonaphthalene derivatives of our invention (taken alone or in combination) added to a tobacco product, either to the filter or to the tobacco section, may be as low as 0.001% based on the weight of the tobacco. The amount of the mono-oxomethyl substituted polyhydrodimethanonaphthalene derivatives added to the tobacco product may be from about 0.001% up to about 0.1% based on the weight of the tobacco, preferably from about 0.005% up to about 0.05%, and more preferably from about 0.01% up to about 0.015%.

The mono-oxomethyl substituted polyhydrodimethanonaphthalene derivatives of our invention may be incorporated at any step into the treatment of the tobacco but it is preferred that they be added either separately or in admixture after the tobacco has been cured, aged and shredded and just prior to the manufacture of the desired tobacco product, for example, cigarettes, cigars, pipe tobacco, or other smoking products. Also, it may be added to tobacco smoke filter material prior to forming the filter rod. The additive is conveniently dissolved in a solvent, such as ethyl alcohol, and applied to the tobacco by spraying, dipping or other methods of application generally employed for treating tobacco. Also, it may be sprayed onto the filter material. Although solutions of this compound are preferred, suspenions thereof may be utilized. Other suitable solvents are, for example, acetone, diethyl ether, n-hexane, or the like. After treatment of the tobacco or the filter with at least one of the mono-oxomethyl substituted polyhydrodimethanonaphthalene derivatives of our invention, substantially all of the solvent is evaporated therefrom prior to its manufacture into tobacco products.

The term "tobacco" will be understood herein to mean the natural products such as, for example, Burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products in which the mono-oxomethyl substituted polyhydrodimethanonaphthalene derivatives of our invention are useful include those designed or used for smoking such as in cigarette, cigar and pipe tobacco, as well as products such as snuff, chewing tobacco, and the like.

The following examples I–X are given to illustrate methods for producing the mono-oxomethyl substituted polyhydrodimethanonaphthalene derivatives of our invention. The examples following Example X are given to illustrate embodiments of the utilization of the mono-oxomethyl substituted polyhydrodimethanonaphthalene derivatives of our invention. It will be understood that these examples are illustrative and that the invention is not to be considered as restrictive to these examples except as indicated in the appended claims.

EXAMPLE I

PREPARATION OF 1,2,3,4,4A,5,5A,8 OCTAHYDRO-1,4:5,8 DIMETHANONAPHTHALENE-2-CARBOXALDEHYDE

Reaction

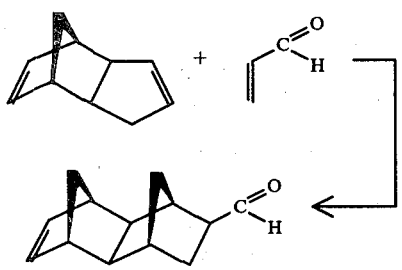

Into a high pressure autoclave are placed the following ingredients:

396 dicyclopentadiene;
252 grams acrolein; and
500 ml toluene

The autoclave is sealed, and with stirring, heated at 225° C. at 200 psig for a period of three hours. At the end of the reaction, the autoclave is opened and a portion of the product is distilled in a "Rushover" apparatus yielding the following fractions:

| Fraction No. | Vapor Temp. (°C.) | Liquid Temp. (°C.) | Vacuum mm. Hg. Pressure | Weight of Fractions (mg) |
|---|---|---|---|---|
| 1 | 23/50 | 23/70 | 50/52 | 911.0 |
| 2 | 56 | 77 | 50 | 802.0 |
| 3 | 68 | 100 | 40 | 1031.0 |
| 4 | 75 | 100 | 30 | 902.0 |
| 5 | 83 | 115 | 15 | 200.0 |
| 6 | 86 | 128 | 15 | 125.1 |
| 7 | 100 | 133 | 10 | 91.6 |
| 8 | 108 | 137 | 10 | 105.5 |
| 9 | 120 | 143 | 8 | 96.0 |
| 10 | 125 | 147 | 8 | 96.5 |
| 11 | 135 | 168 | 2 | 1588.0 |
| 12 | 139 | 186 | 2 | |
| 13 | 156 | 220 | 2 | 339.0 |

Fractions 11 and 12 of this distillation are bulked and the resulting bulked fractions are distilled on a fractionation column yielding the following fractions:

| Fraction No. | Vapor Temp. (°C.) | Liquid Temp. (°C.) | Vacuum mm. Hg. Pressure | Reflux Ratio | Weight of Fractions (mg) |
|---|---|---|---|---|---|
| 1 | 23/77 | 23/122 | 2/2 | 9:1 | 20.8 |
| 2 | 78 | 125 | 2 | 9:1 | 17.3 |
| 3 | 78 | 126 | 2 | 9:1 | 18.9 |
| 4 | 78 | 125 | 2 | 9:1 | 21.3 |
| 5 | 79 | 126 | 2 | 9:1 | 27.8 |
| 6 | 80 | 127 | 2 | 9:1 | 23.5 |
| 7 | 80 | 128 | 2 | 9:1 | 106.5 |
| 8 | 80 | 127 | 2 | 9:1 | 122.4 |
| 9 | 80 | 129 | 2 | 9:1 | 44.0 |
| 10 | 80 | 129 | 2 | 9:1 | 31.1 |
| 11 | 83 | 130 | 2 | 9:1 | 39.0 |
| 12 | 83 | 130 | 2 | 9:1 | 42.4 |
| 13 | 83 | 130 | 2 | 1:1 | 106.4 |
| 14 | 83 | 130 | 2 | 1:1 | 102.3 |
| 15 | 83 | 130 | 2 | 1:1 | 106.9 |
| 16 | 83 | 133 | 2 | 1:1 | 128.1 |
| 17 | 83 | 134 | 2 | 1:1 | 130.1 |
| 18 | 84 | 136 | 2 | 1:1 | 128.7 |
| 19 | 86 | 170 | 2 | 1:1 | 132.0 |
| 20 | 78 | 187 | 2 | 1:1 | 64.2 |
| 21 | 50 | 220 | 2 | 1:1 | 44.1 |

Fractions 14–19 are bulked and have an herbal, strong, green, aldehydic, wormwood-like, floral aroma profile. Bulked fractions 4–14 has a melony, cucumber-like, violet, green, aldehydic aroma profile.

From a flavor standpoint fraction 14 has a sweet, aldehydic, floral, melony, herbaceous aroma and taste profile at 0.0001 ppm. In addition, it is an excellent vanilla flavor enhancer and orange oil flavor enhancer.

FIG. 1 is the GLC profile of the reaction production prior to distillation (conditions: SE-30 packed column, programmed at 220° C. isothermal (¼"×10 feet). The peak indicated on FIG. 1 by the reference "1" is for the reaction product having the structure:

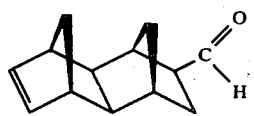

FIG. 2 is the NMR spectrum for the bulked fractions 4–20 of the foregoing distillation product containing the compound having the structure:

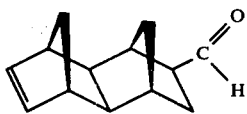

FIG. 3 is the infra-red spectrum for bulked fractions 4–20 of the foregoing distillation product containing the compound having the structure:

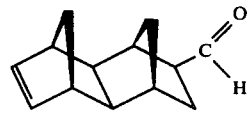

EXAMPLE II

PREPARATION OF DECAHYDRO-1,4:5,8 DIMETHANONAPHTHALENE-2-CARBOXALDEHYDE

Reaction

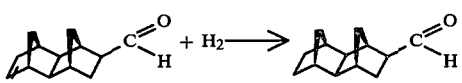

Into a Parr shaker apparatus is placed the following ingredients:

| Ingredients | Parts by Weight |
|---|---|
| Bulked fractions 22-26 of the distillation product of the reaction product of Example I containing the compound having the structure:  | 260 grams (1.3 moles) |
| 1% Palladium on carbon | 3 grams |
| Anhydrous isopropyl alcohol | 80 ml |

The Parr shaker is pressurized with hydrogen to a pressure of between 87 and 109 psig while maintaining the reaction temperature at 48°–54° C. for a period of 14 hours. At the end of this period, the Parr shaker is depressurized, opened and the contents are filtered. The resulting product is then distilled on a fractionation column yielding the following fractions:

| Fraction No. | Vapor Temp. (°C.) | Liquid Temp. (°C.) | Vacuum mm. Hg. Pressure | Weight of Fraction (gm) |
|---|---|---|---|---|
| 1 | 35 | 37 | 20/20 | 13.6 |
| 2 | 119 | 120 | 1 | 10.6 |
| 3 | 122 | 122 | 1 | 15.6 |
| 4 | 127 | 127 | 1 | 15.1 |
| 5 | 127 | 140 | 1 | 16.7 |
| 6 | 127 | 140 | 1 | 16.7 |
| 7 | 127 | 140 | 1 | 18.1 |
| 8 | 127 | 140 | 1 | 19.5 |
| 9 | 127 | 140 | 1 | 16.0 |
| 10 | 127 | 140 | 1 | 15.6 |
| 11 | 127 | 147 | 1 | 17.3 |
| 12 | 127 | 147 | 1 | 21.2 |
| 13 | 127 | 147 | 1 | 22.5 |
| 14 | 130 | 200 | 1 | 22.7 |

Fraction 7–13 of the foregoing distillation are bulked for subsequent evaluation and for subsequent reaction. Fractions 7–13, bulked, from a fragrance standpoint, have a floral, cinnamon-like and melony aroma profile.

FIG. 4 is the GLC profile for the reaction product prior to distillation. (Conditions: SE-30 column programmed at 130°–220° C. at 8° C. per minute).

FIG. 5 is the NMR spectrum for fraction 11 of the foregoing distillation containing the compound having the structure:

FIG. 6 is the infra-red spectrum for fraction 11 of the foregoing distillation containing the compound having the structure:

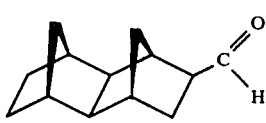

EXAMPLE III

PREPARATION OF DIMETHYL ACETAL OF 1,2,3,4,4A,5,5A,8 OCTAHYDRO-1,4:5,8 DIMETHANONAPHTHALENE-2-CARBOXALDEHYDE

Reaction

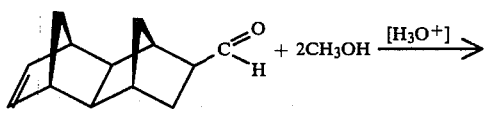

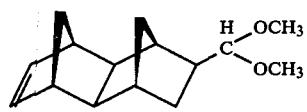

Into a 100 ml reaction flask equipped with stirrer, thermometer, reflux condenser and heating mantle is placed the following:

10.0 grams of the reaction product of Example I, bulked fractions 22–26 containing the compound having the structure:

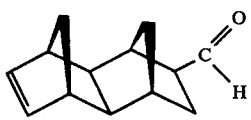

4.0 grams borontrifluoride etherate
25.0 grams anhydrous methyl alcohol

The reaction mass is heated to 60° C. and maintained at 60° C. for a period of three hours.

The reaction product having the structure:

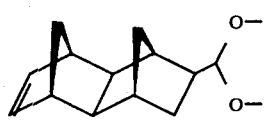

(as confirmed by NMR, IR mass spectral analyses) is trapped via preparative GLC. (Conditions: SE-30 column programmed at 220° C., isothermal)

FIG. 7 is the GLC profile for the reaction product of this example. The peak indicated by the reference "11" is the peak for the staring material, the aldehyde having the structure:

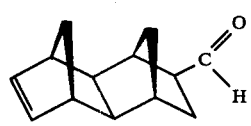

The peak indicated by the reference numeral "12" is for a side-product having the structure:

The peak indicated by the reference numeral "13" is the peak for the reaction product having the structure:

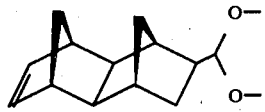

FIG. 8 is the NMR spectrum for the peak "13" of the GLC profile of FIG. 7.

EXAMPLE IV

PREPARATION OF

1,2,3,4,4A,5,8,8A-OCTAHYDRO 1,4:5,8-DIMETHANONAPHTHALENE-2-METHANOL

Reaction

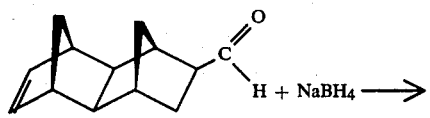

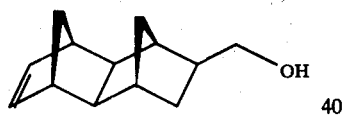

Into a 1 liter reaction flask equipped with stirrer, thermometer, reflux condenser and heating mantle is placed 500 grams of isopropyl alcohol and 60 grams of sodium borohydride. The resulting mixture is heated to 50° C. While maintaining this mixture at 50° C., over a period of one hour 300 grams of the aldehyde produced according to Example I, bulked fractions 22–26 having the structure:

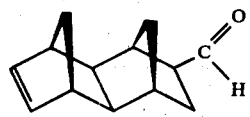

is added to the reaction mass.

The reaction mass is then maintained at 60° C. for a period of 0.5 hours.

The reaction mass is then cooled and washed with 2 liters of water. An aqueous 10% solution of hydrochloric acid is then added until the solution is clear. The reaction mass is then washed and neutralized with sodium carbonate.

The reaction mass is then distilled on a 1"×12" Goodloe column yielding the following fractions:

| Fraction No. | Vapor Temp. (°C.) | Liquid Temp. (°C.) | Vacuum mm. Hg. Pressure | Ratio Reflux | Weight of Fraction (gm) |
|---|---|---|---|---|---|
| 1 | 23/110 | 27/147 | 1/1 | 9:1 | 14.0 |
| 2 | 111 | 147 | 0.8 | 9:1 | 15.3 |
| 3 | 111 | 147 | 0.65 | 9:1 | 20.1 |
| 4 | 111 | 147 | 0.65 | 9:1 | 24.3 |
| 5 | 116 | 153 | 0.65 | 1:1 | 26.1 |
| 6 | 122 | 157 | 0.65 | 1:1 | 27.1 |
| 7 | 122 | 158 | 0.65 | 1:1 | 25.0 |
| 8 | 122 | 161 | 0.65 | 1:1 | 27.4 |
| 9 | 121 | 168 | 0.65 | 1:1 | 26.3 |
| 10 | 119 | 196 | 0.65 | 1:1 | 25.8 |
| 11 | 115 | 230 | 0.65 | 1:1 | 17.6 |
| 12 | 100 | 235 | — | — | — |

Bulked fraction 6–10 of the foregoing distillation have a sandalwood-like, patchouli-like and vetiver-like aroma profile.

FIG. 9 is the GLC profile for bulked fractions 3–11 of of the distillation product of the foregoing reaction product. The peak indicated by the reference numeral "21" is the peak indicating the product having the structure:

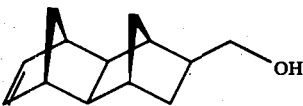

The conditions for the GLC operation are: SE-30 column operated at 220° C. isothermal.

FIG. 10 is the NMR spectrum for bulked fractions 3–11 of foregoing distillation containing the compound having the structure:

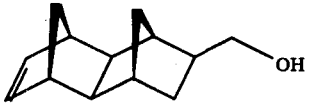

FIG. 11 is the infra-red spectrum for bulked fractions 3–11 of the foregoing distillation containing the compound having the structure:

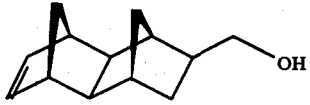

EXAMPLE V

PREPARATION OF

1,4:5,8-DIMETHANONAPHTHALENE-2-METHANOL DECAHYDRO

Reaction

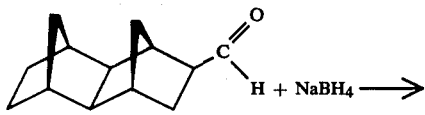

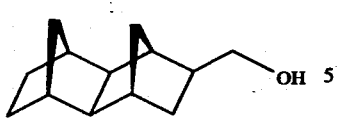

Into a 1 liter reaction vessel equipped with reflux condenser, thermometer, addition funnel, heating mantle and stirrer is placed 500 grams of isopropyl alcohol and 40 grams of sodium borohydride. Over a period of 20 minutes, 280 grams (1.3 moles) of bulked fractions 4-11 of the distillation product of Example II containing the compound having the structure:

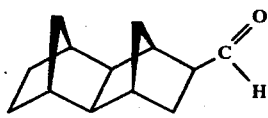

is added to the reaction mass, with refluxing. The reaction mass is maintained at a temperature of 70°-80° C. for a period of 20 hours.

At the end of the 20 hour period 200 ml acetone is added to the reaction mass. Then, 1.5 liters of water is added to the reaction mass and the aqueous phase is separated from the organic phase. The organic phase crystallizes, at room temperature. The organic phase is distilled on a fractionation column yielding the following fractions:

| Fraction No. | Vapor Temp. (°C.) | Liquid Temp. (°C.) | Weight of Fraction (gm) |
|---|---|---|---|
| 1 | 130 | 140 | 16.1 |
| 2 | 130 | 140 | 21.5 |
| 3 | 130 | 140 | 17.3 |
| 4 | 130 | 140 | 22.7 |
| 5 | 130 | 140 | 20.0 |
| 6 | 130 | 140 | 29.9 |
| 7 | 130 | 147 | 28.4 |
| 8 | 130 | 220 | 23.0 |

FIG. 12 is the GLC profile for the reaction product prior to distillation. The peak indicated by the reference numeral "31" is for the reaction product, the compound having the structure:

(Conditions SE-30 column operated at 220° C. isothermal).

FIG. 13 is the NMR spectrum for fraction 8 of the foregoing distillation containing the compound having the structure:

FIG. 14 is the infra-red spectrum for fraction 8 of the foregoing distillation containing the compound having the structure:

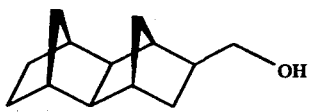

EXAMPLE VI

PREPARATION OF 1,4:5,8-DIMETHANONAPHTHALENE-2-METHANOLDECAHYDRO ACETATE

Reaction

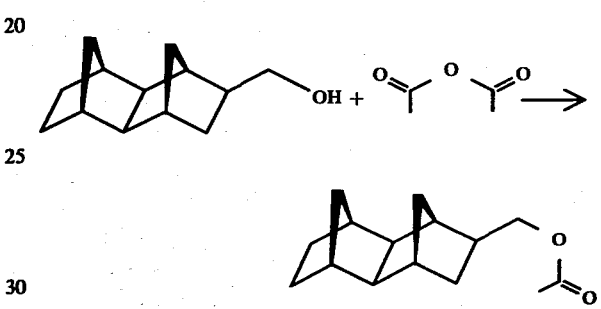

Into a 1 liter reaction flask equipped with stirrer, thermometer, and reflux condenser is placed 160.0 grams of acetic anhydride, 200.0 ml toluene and 178.9 grams of the alcohol reaction product produced according to Example V, bulked fractions 3-8 having the structure:

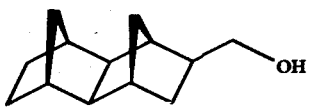

The reaction mass is heated to 116° C. and maintained at 116° C. for a period of 2 hours. At the end of the reaction, 1 liter of water is added to the reaction mass and the organic phase is separated from the aqueous phase. The organic phase is washed with saturated sodium carbonate and the resulting product is fractionally distilled yielding the following fractions:

| Fraction No. | Vapor Temp. (°C.) | Liquid Temp. (°C.) | Vacuum mm. Hg. Pressure | Weight of Fraction (gm) |
|---|---|---|---|---|
| 2 | 147 | 152 | 2 | 19.4 |
| 3 | 137 | 150 | 1 | 14.1 |
| 4 | 135 | 140 | 1 | 14.1 |
| 5 | 120 | 130 | 1 | 17.2 |
| 6 | 117 | 135 | 1 | 21.0 |
| 7 | 117 | 140 | 1 | 24.3 |
| 8 | 120 | 140 | 1 | 18.5 |
| 9 | 127 | 148 | 1 | 15.8 |
| 10 | 128 | 152 | 1 | 23.0 |
| 11 | 131 | 163 | 1 | 10.9 |
| 12 | 134 | 270 | 1 | 11.9 |

Fraction 8-10 are bulked for subsequent evaluation. Fractions 8-10 have a floral, pineapple-like aroma from a perfumery standpoint and a pineapple taste.

FIG. 15 is the GLC profile for the reaction product prior to distillation (Conditions: SE-30 column, programmed at 220° C. isothermal). The peak indicated by the reference numeral "41" is the peak for the reaction product having the structure:

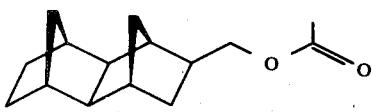

FIG. 16 is the NMR spectrum for fraction 6 of the foregoing distillation containing the compound having the structure:

FIG. 17 is the infra-red spectrum for fraction 6 of the foregoing distillation containing the compound having the structure:

EXAMPLE VII

PREPARATION OF 1,2,3,4,4A,5,8,8A-OCTAHYDRO-1,4:5,8-DIMETHANONAPHTHALENE-2-METHANOL ACETATE

Reaction

Into a 1 liter reaction flask equipped with stirrer, thermometer and reflux condenser are placed 102 grams of acetic anhydride, 500.0 ml toluene and 72.0 grams of the alcohol reaction product produced according to Example IV, bulked fractions 6-10 having the structure:

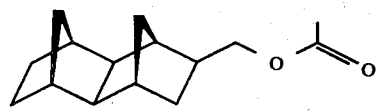

The reaction mass is heated to 117° C. and maintained at 117° C. for a period of 1.5 hours. At the end of the reaction, the toluene solvent is stripped and the reaction mass is washed with concentrated aqueous sodium carbonate. The reaction mass is then distilled on a fractionation column yielding the following fractions:

| Fraction No. | Vapor Temp. (°C.) | Liquid Temp. (°C.) | Weight of Fraction (gm) |
|---|---|---|---|
| 1 | 126 | 180 | 1.9 |
| 2 | 128 | 190 | 6.2 |
| 3 | 130 | 195 | 4.7 |
| 4 | 130 | 200 | 9.2 |
| 5 | 130 | 205 | 3.5 |

Fractions 2-4 are bulked. The bulked fractions from a perfumery standpoint have a sweaty aroma nuance. From a flavor standpoint, bulked fractions 2-4 at a concentration of 1 ppm have a green, artichoke-like aroma and taste profile making it useful for augmenting or enhancing the aroma and taste of salad dressings.

FIG. 18 is the GLC profile of the reaction product of this example containing the compound having the structure:

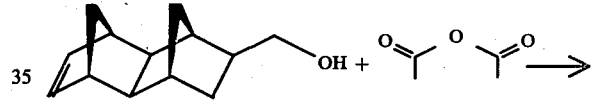

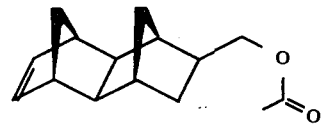

FIG. 19 is the NMR spectrum for fraction 4 of the foregoing distillation containing the compound having the structure:

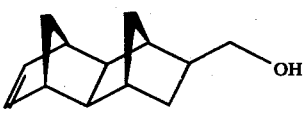

FIG. 20 is the infra-red spectrum for fraction 4 of the foregoing distillation product containing the compound having the structure:

EXAMPLE VIII

PREPARATION OF DIMETHYL 1,2,3,4,4A,5,8,8A-OCTAHYDRO-1,4:4,8-DIMETHANONAPHTHALENE-2-CARBOXALDEHYDE

Reaction

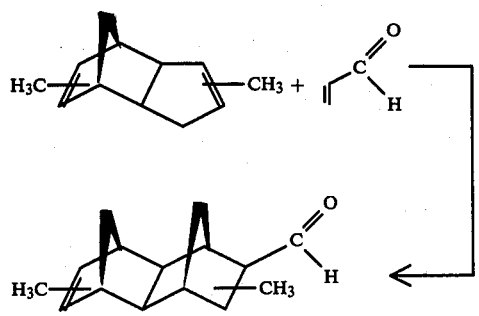

Into a 2 liter autoclave is placed the following materials:
(a) 400 grams of methyl cyclopentadiene dimer, a mixture of compounds defined according to the structures:

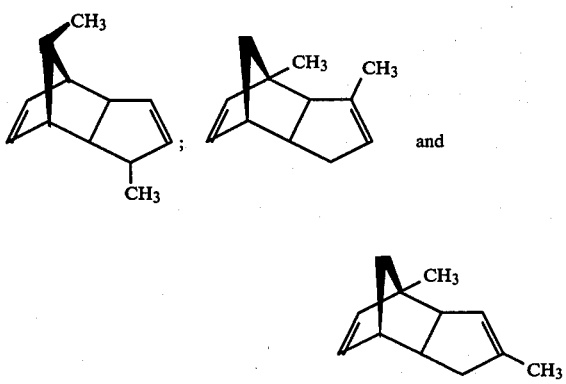

(b) 200 grams acrolein; and
(c) 300 ml toluene.

The autoclave is sealed and heated to 225° C. (180 psig) and maintained at that temperature and pressure for a period of two hours. At the end of the two hour period, the autoclave is depressurized and opened. The reaction product is analyzed via GLC, NMR, IR and mass spectral analyses. The resulting product has an animalic, leafy, green, herbaceous, floral (violet-like) aroma with cinnamon-like and cucumber undertones from a fragrance standpoint. The resulting substance has a green, melony, minty, herbaceous and floral aroma and taste profile at 2 ppm making it useful for mint and peppermint flavors.

FIG. 21 is the GLC profile for the reaction product. The peak indicated by the reference numeral "51" is the peak for the reaction product defined according to the structures:

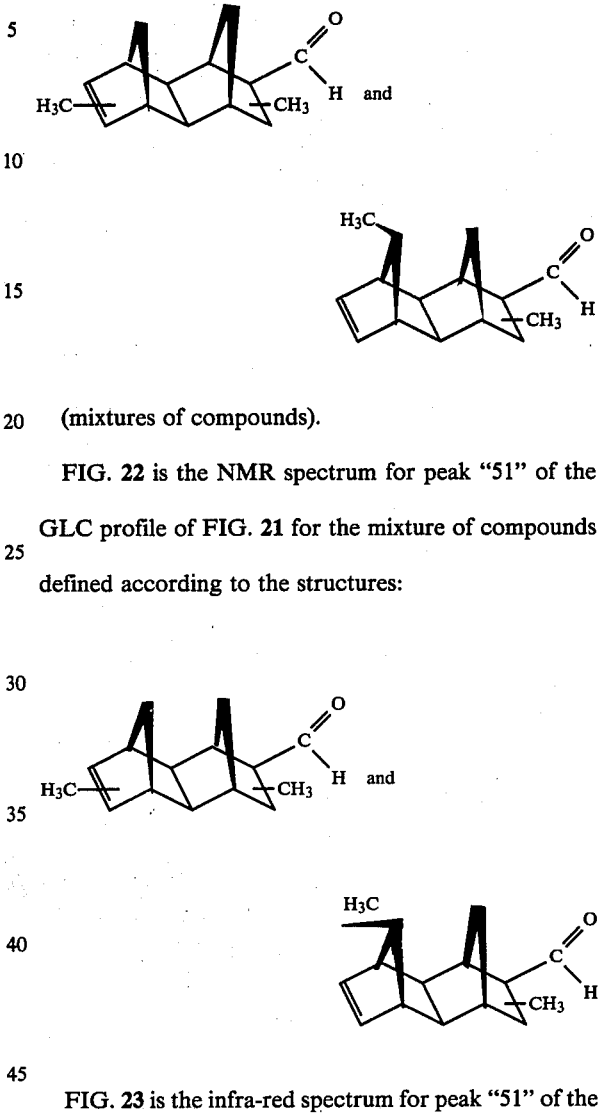

(mixtures of compounds).

FIG. 22 is the NMR spectrum for peak "51" of the GLC profile of FIG. 21 for the mixture of compounds defined according to the structures:

FIG. 23 is the infra-red spectrum for peak "51" of the GLC profile of FIG. 21 for the mixture of compounds defined according to the structures:

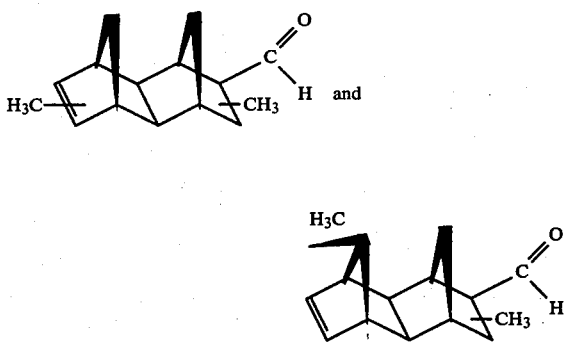

EXAMPLE IX

PREPARATION OF 1,2,3,4,4A,5,8,8A-OCTAHYDRO-3-METHYL-1,4:5,8 DIMETHANONAPHTHALENE-2-CARBOXALDEHYDE

Reaction

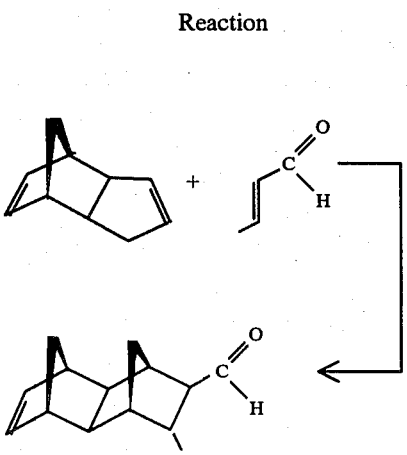

Into a 2 liter autoclave is placed the following materials:

(a) Dicyclopentadiene: 400 grams (b) Crotonaldehyde: 255 grams (c) Toluene: 500 ml The autoclave is sealed and heated to 225° C. at a pressure of 200-320 psig and maintained at a temperature of 25° C. at a pressure in the range of 200-320 psig for a period of three hours. At the end of the three hour period, the autoclave is depressurized and opened. The reaction mass is then distilled on a fractionation column yielding a product boiling at a temperature in the range of 92°-96° C. (vapor temperature) and a liquid temperature in the range of 126°-140° C. at 1.0 mm/Hg pressure.

The reaction product at that boiling point has a spicy, cinnamon-like aroma.

FIG. 24 is the GLC profile for the reaction product (conditions: SE-30 column programmed at 220° C. isothermal).

FIG. 25 is the NMR spectrum for the resulting reaction product at the foregoing boiling range.

FIG. 26 is the infra-red spectrum for the resulting reaction product at the above boiling range.

EXAMPLE X

PREPARATION OF 1,2,3,4,4A,5,8,8A-OCTAHYDRO-2-METHYL-1,4:5,8-DIMETHANONAPHTHALENE-2-CARBOXALDEHYDE

Reaction

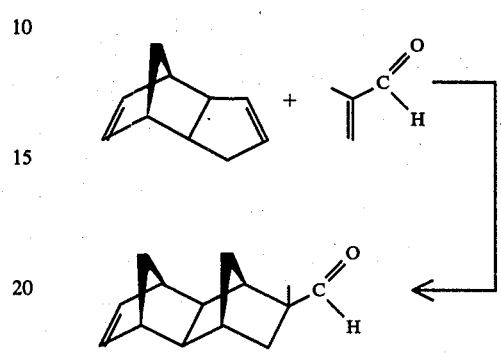

Into a 200 ml autoclave is placed the following ingredients:

(i) 400 grams Dicyclopentadiene;
(ii) 255 grams of methacrolein; and
(iii) 500 ml toluene The autoclave is sealed and heated to 225° C. and maintained at 225° C. and at a pressure of 200 psig for a period of three hours. At the end of the three hour period the autoclave is opened and the resulting product is fractionally distilled yielding the following fractions:

| Fraction No. | Vapor Temp. (°C.) | Liquid Temp. (°C.) | Vacuum mm.Hg. Pressure | Reflux Ratio | Weight of Fraction (gm) |
|---|---|---|---|---|---|
| 1 | 27/57 | 23/90 | 2/2 | 9:1 | 21.1 |
| 2 | 70 | 126 | 2 | 9:1 | 11.5 |
| 3 | 75 | 132 | 2 | 9:1 | 13.7 |
| 4 | 83 | 135 | 2 | 9:1 | 17.2 |
| 5 | 83 | 135 | 2 | 9:1 | 13.5 |
| 6 | 85 | 136 | 2 | 9:1 | 23.5 |
| 7 | 85 | 136 | 2 | 9:1 | 24.8 |
| 8 | 85 | 136 | 2 | 9:1 | 26.1 |
| 9 | 85 | 176 | 2 | 9:1 | 18.7 |
| 10 | 86 | 136 | 2 | 9:1 | 17.8 |
| 11 | 86 | 136 | 2 | 1:1 | 33.1 |
| 12 | 86 | 137 | 2 | 1:1 | 30.6 |
| 13 | 86 | 137 | 2 | 1:1 | 29.8 |
| 14 | 86 | 137 | 2 | 1:1 | 31.3 |
| 15 | 86 | 137 | 2 | 1:1 | 32.0 |
| 16 | 86 | 140 | 2 | 1:1 | 33.1 |
| 17 | 86 | 140 | 2 | 1:1 | 29.6 |
| 18 | 86 | 140 | 2 | 1:1 | 29.0 |
| 19 | 87 | 140 | 2 | — | 32.1 |
| 20 | 85 | 143 | 2 | — | 33.3 |
| 21 | 80 | 186 | 2 | — | 30.1 |

Fractions 4-15 are bulked for subsequent evaluation for tabacco, food flavoring and fragrance properties.

EXAMPLE XI

CHYPRE PERFUME FORMULATIONS

The following formulation is prepared:

| Ingredients | Parts by Weight |
|---|---|
| Texas Cedarwood Oil | 200 |
| Patchouli Oil | 50 |

-continued

| Ingredients | Parts by Weight |
|---|---|
| Vetivar Oil | 30 |
| Bergamot Oil | 150 |
| African Geranium Oil | 50 |
| Coumarin | 60 |
| Natural Oak Moss | 80 |
| Tolu Balsam Peru | 200 |
| Labdanum | 150 |
| Musk Xylene | 10 |
| Product of Example IV, bulked fractions 6-10 consisting of the compound having the structure: 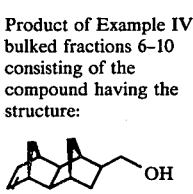 | 135 |

The addition of the compound having the structure:

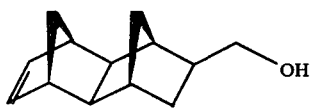

to this Chypre essence causes said Chypre to have an interesting sandalwood-like, patchouli-like and vetiver-like series of topnotes.

Accordingly, this formulation can be described as having a Chypre essence with patchouli-like, sandalwood-like and vetiver-like topnotes.

EXAMPLE XII

PREPARATION OF HERBAL FRAGRANCES

The following mixtures are prepared:

TABLE I

| Ingredients | Parts by Weight | | | |
|---|---|---|---|---|
| | XIIA | XIIB | XIIC | XIID |
| Amyl Cinnamic Aldehyde | 20% | 20% | 20% | 20% |
| Phenyl Acetaldehyde Dimethyl Acetal | 4% | 4% | 4% | 4% |
| Thyme Oil, White | 8% | 8% | 8% | 8% |
| Sauge Sclaree French | 8% | 8% | 8% | 8% |
| Galbanum Oil | 4% | 4% | 4% | 4% |
| Geranyl Acetate | 10% | 10% | 10% | 10% |
| Juniper Berry Oil | 4% | 4% | 4% | 4% |
| Methyl Octin Carbonate | 2% | 2% | 2% | 2% |
| Linalyl Acetate | 10% | 10% | 10% | 10% |
| Dihydro Methyl Jasmonate | 20% | 20% | 20% | 20% |
| Fenchyl Ethyl Ether | 10% | 10% | 10% | 10% |
| Aldehyde produced according to Example I having the structure: 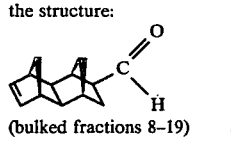 (bulked fractions 8-19) | 3% | 0% | 0% | 0% |

TABLE I-continued

| Ingredients | Parts by Weight | | | |
|---|---|---|---|---|
| | XIIA | XIIB | XIIC | XIID |
| Reaction product of Example II having structure: (bulked fractions 7-13) | 0% | 6% | 0% | 0% |
| Product produced according to Example VI having the structure: (bulked fractions 8-10) | 0% | 0% | 6% | 0% |
| Product produced according to Example VIII, a mixture of compounds defined according to the structures: | 0% | 0% | 0% | 5% |

When added to this herbal formulation the product of Example I imparts to the herbal formulation a melony, cucumber, violet-like, wormwood-like and generally pleasant floral undertone.

The product of Example II when added to this herbal formulation imparts to it, a floral, melony and cinnamon-like undertones.

When the product of Example VI is added to this herbal formulation a pineapple-like, pleasant floral undertone is added to the herbal essence profile.

When the reaction product of Example VIII is added to this herbal formulation, animalic, leafy, floral, violet-like, cinnamon-like and cucumber-like undertones are imparted to this formulation.

EXAMPLE XIII

PATCHOULI/SPICY PERFUME FORMULATION

The following mixture is prepared:

| Ingredients | Parts by Weight |
|---|---|
| Orange Oil | 50 |
| Beramot Oil | 20 |
| Lime Oil | 100 |
| 1-Hydroxy-methyl-2,4,6 Trimethyl cyclohexane | 45 |
| Neroli Oil | 5 |
| 4-(4-Methyl-4-Hydroxyamyl) Δ³-cyclohexene carboxaldehyde | 10 |
| 2,3,3A,4,5,7A-Hexahydro-6,7A,8,8- | |

-continued

| Ingredients | Parts by Weight |
|---|---|
| | 100 |
| Tetramethyl-1,5-methanol-[1H]-inden-1-ol 1',2',3',4',5',6',7',8'-octahydro 2',3',8',8'-tetramethyl-2'-acetonaphthone isomer mixture produced according to the process of Example VII of the U.S. Letters Pat. No. 3,911,018 issued on October 7, 1975 | 20 |
| Gamma Methyl Ionone | 20 |
| 1-acetyl-2,5,5-trimethylcycloheptane | 100 |
| Substituted tricylcodecane derivatives prepared according to Example XII of U.S. Pat. No. 4,275,251 issued on June 23, 1981 | 100 |
| Product of Example IX, supra, having the structure: | 85 |

The compound produced according to Example IX having the structure:

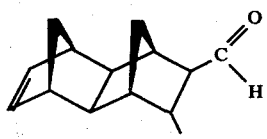

imparts to this patchouli/spicy formulation an intense, cinnamon-like, long lasting, oriental, spicy characteristic.

EXAMPLE XIV

PREPARATION OF SOAP COMPOSITION

A total of 100 grams of soap chips produced from unperfurmed sodium base toilet soap made from talo and coconut oil is admixed with 1 gram of each of the perfume compositions set forth in Table II, below until a substantially homogeneous composition is obtained. The mixture is melted under 8 atmospheres pressure at 190° C. and maintained at 190° C. with mixing for a period of five hours at 8 atmospheres pressure. At the end of the five hour period, the resulting mixture is cooled and cut into soap bars. Each of the soap bars manifest an excellent aroma as set forth in Table II, supra:

TABLE II

| Structure of Compound and example by which produced | Perfumery Profile |
|---|---|
| Aldehyde produced according to Example I, bulking fractions 14-19, having the structure: 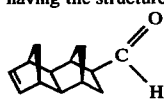 | An herbal, strong, green, aldehydic, wormwood-like and floral aroma profile. |
| Compound produced according to Example I, having the structure: bulked fractions 8-12. | A melony, cucumber-like, violet-like, green, aldehydic aroma profile. |
| Compound produced according to Example II, having the structure: bulked fractions 7-13. | A floral, melony, cinnamon-like aroma. |
| Compound produced according to Example IV, having the structure: bulked fractions 6-10. | A sandalwood, patchouli, vetiver aroma profile. |
| Compound produced according to Example VI, having the structure: bulked fractions 8-10. | A floral, pineapple-like aroma profile. |
| Compound produced according to Example VII, having the structure: bulked fractions 1-5. | |
| A mixture of compounds produced according to Example VIII, containing the compounds having structures: and | An animalic, leafy, green, herbaceous, floral, violet-like aroma with cinnamon-like and cucumber-like undertones. |
| Compound produced according to Example IX having the structure: | A spicy, cinnamon-like aroma profile. |
| Perfume composition of Example XI. | A chypre aroma with patchouli-like, vetiver-like and sandalwood-like topnotes. |
| Perfume composition of Example XIIA. | A herbal aroma with melony, cucumber, violet-like, wormwood-like and pleasant |

TABLE II-continued

| Structure of Compound and example by which produced | Perfumery Profile |
|---|---|
| | floral undertones. |
| Perfume composition of Example XIIB. | A herbal aroma with floral, melony and cinnamon-like undertones. |
| Perfume composition of Example XIIC. | A herbal aroma with floral and pineapple-like undertones. |
| Perfume composition of Example XIID. | A herbal essence with animal-like, leafy, floral, violet-like, cinnamon-like and cucumber undertones. |
| Perfume composition of Example XIII. | A patchouli/spicy formulation an intense, cinnamon-like, long lasting, oriental, spicy characteristic. |

EXAMPLE XV

PREPARATION OF A DETERGENT COMPOSITION

A total of 100 grams of a detergent powder sold under the trademark "RINSO ®" are mixed with 0.15 grams of each of the perfumery substances as set forth in Table II of Example XIV, supra, until a substantially homogeneous composition is obtained. Each of the detergent powders manifest an excellent aroma as set forth in Table II of Example XIV.

EXAMPLE XVI

PREPARATION OF COSMETIC BASES

A cosmetic powder is prepared by mixing in a ball mill 100 grams of talcum powder with 0.25 grams of one of the perfumery substances as set forth in Table II of Example XIV. The cosmetic powders produced using the materials of Table II of Example XIV have aroma characteristics as set forth in Table II of Example XIV.

EXAMPLE XVII

LIQUID DETERGENT COMPOSITION

Concentrated liquid detergents with aromas as set forth in Table II of Example XIV containing 0.2%, 0.5% and 1.2% of one of the substances set forth in Table II of Example XIV are prepared by adding appropriate quantities of perfumery substances as set forth in Table II of Example XIV to a liquid detergent known as P-87. The aroma intensity of each of the liquid detergents so prepared increases with increasing concentration of each of the substances as set forth in Table II of Example XIV, each of the detergents manifesting aromas as set forth in Table II of Example XIV.

EXAMPLE XVIII

PREPARATION OF COLOGNES AND HANDKERCHIEF PERFUMES

Each of the perfume substances of Table II of Example XIV are incorporated into 80%, 85%, 90% and 95% foodgrade ethanol solutions at the rates of 2.0%, 2.5%, 3.0%, 3.5% and 4.0%; and into handkerchief perfumes at concentrations of 15%, 20%, 25%, 30% and 40% (in 80%, 85%, 90% and 95% aqueous foodgrade ethanol). These of each of the substances of Table II of Example XIV are for distinct and definitive aroma nuances in each of the handkerchief perfumes and colognes as indicated in Table II of Example XIV.

EXAMPLE XIX

PREPARATION OF DETERGENT COMPOSITION

A total of 100 pounds of a detergent powder prepared according to U.S. Pat. No. 4,058,472 (the disclosure of which is incorporated by reference herein) and containing 5% by weight of the sodium salts of a mixture of sulfonated $C_{14}$-$C_{18}$ alkyl catechol as a surface active component, the mixture being 60 parts by weight of mono-$C_{14}$-$C_{18}$ alkyl catechol and 40 parts by weight of di-$C_{14}$-$C_{18}$ alkyl catechol, 35% of sodium tetrapyrophosphate, 30% of sodium silicate, 20% of sodium carbonate, 3% of sodium carboxymethyl cellulose and 7% of starch is mixed with 0.15 grams of one of the perfumery substances set forth in Table II of Example XIV, supra, until substantially homogeneous compositions are obtained. Each of the compositions have excellent aromas as set forth in Table II of Example XIV.

EXAMPLE XX

Scented polyethylene pellets having pronounced aromas as set forth in Table II of Example XIV are prepared as follows:

75 Pounds of polyethylene of a melting point of about 220° F. are heated to about 230° C. under 5 atmospheres pressure in a pressure vessel. 25 Pounds of each of the substances set forth in Table II of Example XIV, separately, are then quickly added to the liquified polyethylene. The temperature is maintained at 230° C. under high pressure and the mixing is continued for about 15 minutes in each case. The pressure vessel is then depressurized and the molten polyethylene enriched with each of the perfumery substances is permitted to exit from the vessel by gravity. The liquid falling through orifices (in the apparatus) in droplets solidifies almost instantaneously on impact with a moving cooled conveyor operating immediately below the pressure vessel. Solid polyethylene pellets having pronounced aromas as set forth in Table II of Example XIV are thus formed. In each case 50 pounds of thus-formed master pellets are then added to 1000 pounds of unscented polyethylene powder and the mass is heated to the liquid state. The liquid is molded into thin sheets, films and container shapes. The thin sheets, films and container shapes have pronounced aromas as set forth in Table II of Example XIV.

EXAMPLE XXI

Utilizing the procedure of Example I at column 15 of U.S. Pat. No. 3,632,396 (the specification for which is incorporated by reference herein), a non-woven cloth substrate useful as a drier-added fabric softening article of manufacture is prepared wherein the substrate, the substrate coating and the outer coating and the perfuming material are as follows:

1. a water dissolvable paper as the substrate ("Dissolvo Paper");
2. Adogen 448 (melting point 140° F.) as the substrate coating; and
3. an outer coating having the following formulation (melting point about 150° F.):
   57% $C_{20-22}$ HAPS
   22% isopropyl alcohol
   20% antistatic agent 1% of one of the perfumery substances as set forth in Table II of Example XIV.

A fabric softening composition prepared as set forth above having aroma characteristics as set forth in Table II of Example XIV consists of a substrate having a weight of about 3 grams per 100 square inches, a substrate coating weighing about 1.85 grams per 100 square inches of substrate and an outer coating weighing about 1.4 grams per 100 square inches of substrate is created, thereby providing a total aromatized substrate and outer coating weight ratio of about 1:1 by weight of the substrate. The aromas as set forth in Table II of Example XIV is imparted in pleasant manners to head spaces in the dryers on operation thereof using the drier-added fabric softening non-woven fabric articles.

EXAMPLE XXII

VANILLA FLAVOR

The following formulation is prepared:

| | |
|---|---|
| Vanillin | 10.0 grams |
| Ethyl Vanillin | 3.0 grams |
| Benzodihydropyrone | 3.0 grams |
| Heliotropin | 1.0 grams |
| Propenyl Guiacol | 0.5 grams |
| Gamma Nonyl Lactone | 0.25 grams |
| Gamma Undecalactone | 0.25 grams |
| Delta-Dodecalactone | 0.25 grams |
| The aldehyde compound of Example I, having the structure: 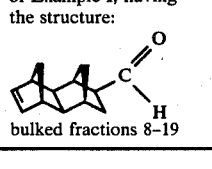 bulked fractions 8–19 | 0.001 grams |

The compound having the structure:

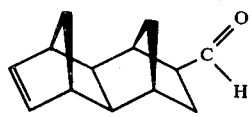

enhances the foregoing vanillin formulation (a) making it more natural-like; and (b) making it three times (3×) as powerful as the formulation without this compound added thereto. In addition, the formulation is rendered much more outstanding in a standard creme-de-Kahlua formulation causing the creme-de-Kahlua formulation to be more natural-like and preferred by a bench panel of five members, unanimously. The resulting formulation containing the compound having the structure:

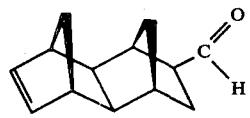

is added to the following liqueur formulation:

| Ingredients | Parts by Weight |
|---|---|
| Clove essential oils | 780 |
| Lemon essential oils | 400 |
| Orange essential oils | 300 |
| Cinnamon essential oils | 250 |
| Mace essential oils | 180 |
| Vanillin formulation (as set forth above) | 150 |
| Neroli essential oil | 10 |
| Citronellol | 2 |
| Rose absolute | 1 |
| Food grade ethanol | 927 |

The resulting liqueur is added to the following mixture in order to produce a consumable material:

| Ingredients | Parts by Weight |
|---|---|
| 96% Food grade ethanol | 301 kg |
| Sugar | 40 kg |
| Distilled water | 46.8 liters |
| Flavor (as set forth above) (0.5% in food grade ethanol) | 0.5 kg |

The resulting liquer has an interesting, bitter almond taste and aroma making it useful as such or as a "Bagne" for a sauce used for soaking pound cakes such as "Rum BaBa".

EXAMPLE XXIII

The vanilla flavor of Example XII is placed into an ice cream mix at the rate of 0.05%. The resulting previously-unflavored ice cream has an excellent vanilla flavor.

EXAMPLE XXIV

SALAD DRESSING

To a portion of essentially flavorless salad dressing, the compound of Example VII, having the structure:

(bulked fractions 1–5) is added at the rate of 1 ppm and also at the rate of 2ppm. The resulting mixtures have characteristic artichoke notes. The salad dressing is a mixture of the following:

| Ingredient | Parts by Weight |
|---|---|
| Black pepper oil | 3 |
| Nutmeg oil | 3 |
| Celery Oil | 3 |
| Lemon oil | 3 |
| Mustard oil | 1 |
| Vinegar-citric acid (50-50 mixture) | 120 |
| Starch paste prepared from tapioca flour-water (50-50 mixture) | 300 |
| Liquid egg yolks | 210 |
| Sodium chloride | 7 |
| Sucrose | 10 |
| Mustard | 20 |
| Locust Bean gum | 6 |

EXAMPLE XXV(A),(B)

LEMON/FRUITY FLAVOR FORMULATION

The following lemony, fruity flavor formulations are prepared:

| Ingredient | Parts by Weight XXV(A) | Parts by Weight XXV(B) |
|---|---|---|
| Natural Lemon Oil, Terpeneless | 10.0 | 10.0 |
| Acetaldehyde | 0.6 | 0.6 |
| Alpha-terpineol | 2.1 | 2.1 |
| Citral | 1.8 | 1.8 |
| Carvone | 0.24 | 0.24 |
| Terpinolene | 1.2 | 1.2 |
| Alpha-terpinene | 0.25 | 0.25 |
| Diphenyl | 0.25 | 0.25 |
| Alpha Fenchyl Alcohol | 0.25 | 0.25 |
| Limonene | 0.35 | 0.35 |
| Linalool | 0.25 | 0.25 |
| Geranyl Acetate | 0.25 | 0.25 |
| Nootkatone | 0.25 | 0.25 |
| Neryl Acetate | 0.25 | 0.25 |
| Geranyl nitrile | 0.55 | 0.55 |
| Citronellyl nitrile | 0.60 | 0.60 |
| Fenchyl ethyl ether | 0.05 | 0.05 |
| The compound of Example II having the structure: 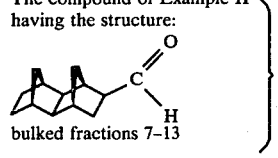 bulked fractions 7-13 | 0.50 | 0.0 |
| The compound of Example VI having the structure: 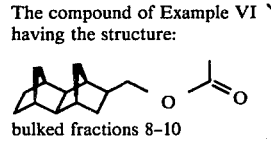 bulked fractions 8-10 | 0.0 | 0.75 |

The compound of Example II adds to this lemon flavor formulation an excellent melony flavor causing the overall formulation to have a "lemon/melon" aroma and taste causing it to be useful in enhancing the taste of fresh papaya fruit when three or four drops of this flavor diluted at the rate of 1% in 50% aqueous foodgrade ethanol is placed on the open papaya fruit.

The compound of Example VI adds an excellent pineapple aroma and taste nuance to this lemon flavor. When the flavor (in 2% dilution and 50% foodgrade ethanol) is added to cooking chicken, the resultant cooked chicken has an excellent "lemony nuance" which is enhanced by use of the compound of Example VI.

EXAMPLE XXVI

ROOT BEER BEVERAGE

The compound having the structure:

produced according to Example IV, bulked fractions 6-10 is added to root beer (Barrelhead, produced by Canada Dry Corporation of Maspeth, New York, a division of the Norton Simon Corporation) at the rate of 1.5 ppm and submitted to a bench panel. The tetracyclic carbinol improves the woody rooty notes insofar as the aroma and taste of the rootbeer are concerned. Therefore, the beverage containing the compound defined according to the structure:

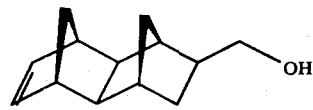

is preferred by a bench panel (of five members) unanimously over the beverage which does not contain the tetracyclic carbinol derivative produced according to Example IV.

EXAMPLE XXVII

AMARETTO FLAVOR

The following formulation is prepared:

| Ingredients | Parts by Weight |
|---|---|
| Lavender essential oil | 105.0 |
| Clary sage essential oil | 100.0 |
| Rosemary essential oil | 100.0 |
| Thyme essential oil | 90.0 |
| Fennel essential oil | 40.0 |
| Mint essential oil | 20.0 |
| Mixture of compounds prepared according to Example VIII having the structures: 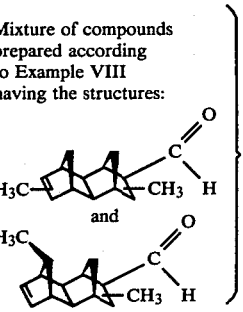 | 5.9 |
| Angelica essential oil | 5.0 |
| Anise essential oil | 5.0 |
| Lemon essential oil | 4.0 |
| Wormwood essential oil | 2.0 |
| Cinnamon essential oil (10% in alcohol solution) | 0.1 |
| Aqueous 95%, foodgrade ethanol | 523.0 |

The mixture of compounds produced according to Example VIII enhances this amaretto flavor in view of the green, melony, minty, herbaceous and floral aroma and taste nuances which particularly enhance the mint oil aroma and taste portion of this formulation.

A liqueur is produced by using the foregoing formulation as follows:

| Ingredient | Parts by Weight |
|---|---|
| 96% alcohol | 46.1 l |
| Sugar | 1.0 kg |
| Distilled Water | 55.1 l |
| Amaretto flavor produced, supra (diluted at the rate of 0.8% in 95% aqueous | 0.5 kg |

| Ingredient | Parts by Weight |
|---|---|
| foodgrade ethanol) | |

In addition, the wormwood essential oil component of the foregoing amaretto flavor can be replaced totally by the use of the compound of Example I having the structure:

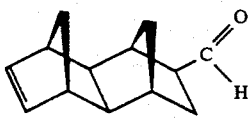

bulked fractions 8–19. Actually the aldehyde having the structure:

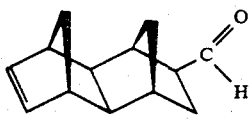

can replace the 2 parts by weight of wormwood essential oil by using only 0.02 parts by weight of the aldehyde having the structure:

EXAMPLE XXVIII

TOOTHPASTE FLAVOR FORMULATION

The following basic toothpaste flavor formulation is prepared:

| Ingredients | Parts by Weight |
|---|---|
| Cardamon Oil | 0.2 |
| Clove Oil | 1.0 |
| Spearmint Oil | 2.0 |
| Peppermint Oil | 96.8 |

This flavor formulation is divided into three portions. To the first portion, nothing is added. To the second portion, 8 parts by weight of the first portion is combined with 2 parts by weight of anethole. Eight parts by weight of the third portion of this flavor is then combined with 2 parts by weight of the compound of Example IX having the structure:

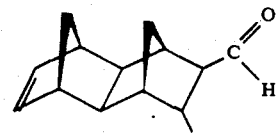

prepared according to Example IX and 2 parts by weight of anethole.

Each of the three flavors are compared in water at the rate of 10 ppm and evaluated by a bench panel. Each of the second and third flavors has sweet anise-like characteristics, but the flavor containing the compound defined according to the structure:

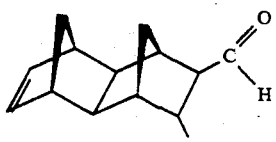

also has cinnamic and spicy aroma and taste nuances. Therefore, the flavor containing the aldehyde produced according to Example IX is preferred over flavors not containing the aldehyde of Example IX and, in addition, the aldehyde of Example IX having the structure:

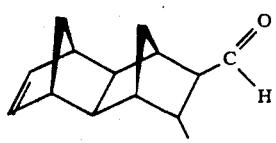

augments and enhances the anise-like flavor.

EXAMPLE XXIX

MINT FLAVOR FORMULATION

The following mint flavor formulation is prepared:

| Ingredients | Parts by Weight |
|---|---|
| Peppermint Oil | 60.0 |
| Spearmint Oil | 38.0 |
| Mixture of compounds produced according to Example VIII having the structures: 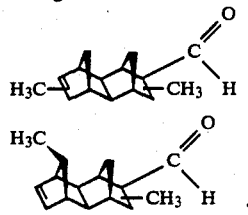 | 2.0 |

The mixture of compounds produced according to Example VIII imparts a minty, herbaceous, floral, green and melony aroma and taste nuance of great intensity to this mint flavor formulation.

EXAMPLE XXX

A. POWDER FLAVOR FORMULATION

20 Grams of the flavor composition of Example XXIX is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F. and a wheel speed of 50,000 rpm.

B. SUSTAINED RELEASE FLAVOR

The following mixture is prepared:

| Ingredients | Parts by Weight |
|---|---|
| Liquid mint Flavor Composition of Example XXIX | 20.0 |
| Propylene glycol | 9.0 |
| Cab-O-Sil ® M-5 (Brand of Silica produced by the Cabot Corporation of 125 High Street, Boston, Mass. 02110; Physical Properties: Surface Area: 200 m$^2$gm Nominal particle size: 0.012 microns Density: 2,3lbs/cu.ft.) | 5.00 |

The Cab-O-Sil is dispersed in the liquid mint flavor composition of Example XXIX with vigorous stirring, thereby resulting in a viscous liquid. 71 Parts by weight of the powder flavor composition of Part A of this example, supra, is then blended into the said viscous liquid, with stirring, at 25° C. for a period of 30 minutes resulting in a dry, free flowing sustained release flavor powder.

EXAMPLE XXXI

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XXIX is added to the solution which is then homogenized to form an emulsion having particle size typically in the range of 5–40 microns. This material is kept at 120° F. under which conditions the gelatin will not jell.

Coacervation is induced by adding slowly and uniformly 40 parts by weight of a 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XXXII

CHEWING GUM

100 Parts by weight of chicle are mixed with 4 parts by weight of the flavor prepared in accordance with Example XXIX. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting mint flavors.

EXAMPLE XXXIII

CHEWING GUM

100 Parts by weight of chicle are mixed with 18 parts by weight of the flavor prepared in accordance with Example XXX(B). 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting mint flavor.

EXAMPLE XXXIV

TOOTHPASTE FORMULATION

The following separate groups of ingredients are prepared:

| Parts by Weight | Ingredients |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalsium Phosphate (Dihydrate) |
| Group "C" | |
| 2.000 | Sodium N—Lauroyl Sarcosinate (foaming agent) |
| Group "D" | |
| 1.200 | Flavor Material of Example XXX(B) |
| 100.00 TOTAL | |

PROCEDURE

1. The ingredients in Group "A" are stirred and heated in a steam jacketed kettle to 160° F.;
2. Stirring is continued for an additional three to five minutes to form a homogeneous gel;
3. The powders of Group "B" are added to the gel, while mixing, until a homogeneous paste is formed;
4. With stirring, the flavor of "D" is added and lastly the sodium-n-lauroyl sarcosinate; and
5. The resultant slurry is then blended for one hour. The completed paste is then transferred to a three roller mill and then homogenized, and finally tubed.

The resulting toothpaste when used in a normal toothbrushing procedure yields a pleasant mint flavor, of constant strong intensity throughout said procedure (1–1.5 minutes).

EXAMPLE XXXV

CHEWABLE VITAMIN TABLETS

The flavor material produced accoding to the process of Example XXX(B) is added to a Chewable Vitamin Tablet. Formulation at a rate of 10 gm/Kg which Chewable Vitamin Tablet formulation is prepared as follows:

In a Hobart mixer, the following materials are blended to homogeneity:

| | Gms/1000 Tablets |
|---|---|
| Vitamin C (ascorbic acid) as Ascorbic acid-sodium ascorbate | 70.11 |

-continued

|  | Gms/1000 Tablets |
|---|---|
| mixture 1:1 | |
| Vitamin $B_1$ (thiamine mononitrate) as Rocoat ® thiamine mononitrate 33⅓% (Hoffman LaRoche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% | 6.6 |
| d-Biotin | 0.044 |
| Flavor of Example XXX(B) | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 gm dry Vitamin A Acetate and 0.6 gm Vitamin D are then added as beadlets. The entire blend is then compressed using concave punches at 0.5 gm each.

Chewing of the resultant tablets yields a pleasant, long-lasting mint flavor for a period of 15 minutes.

EXAMPLE XXVI

CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn Syrup | 60.0 |
| Licorice | 10.0 |
| Glycerine | 20.0 |
| Fig Juice | 4.6 |
| Prune Juice | 5.0 |
| Mint flavor of Example XXX(I) | 0.08 |

The resultant product is redried to a moisture content of 20%. On chewing, this tobacco has an excellent cooling mint flavor nuance in conjunction with the tobacco notes.

EXAMPLE XXXVI

TOBACCO FORMULATION

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is ued in producing cigarettes, and the following formulation is compounded and incorporated into each of these cigarettes:

| Ingredient | Parts by Weight |
|---|---|
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigaretts at the rate of 0.1%.

One-fourth of these model cigaretts are treated in the tobacco section with the mixture of aldehydes produced according to Example VIII having the structures:

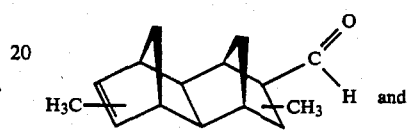

and

One-fourth of these model cigarettes are treated in the tobacco section with the compound defined according to the structure:

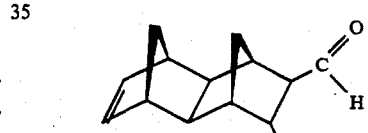

produced according to Example IX.

Each of the foregoing aldehydes is added at rates of 100, 200 and 300 ppm per cigarette.

Another one-fourth of these model cigarettes are treated in the filter with either the mixture of aldehydes of Example VIII or the aldehyde of Example IX at the rate of $2 \times 10^{-5}$ gm per gm of filter.

When evaluated by paired comparison, the cigarettes treated both in the tobacco and the filter with the mixture of compounds produced according to Example VIII are found, in smoke flavor, to have sweet, floral, green, herbaceous, minty and cooling aroma and taste nuances, and also cause the tobacco to be more natural-like. Also an excellent hay tobacco aroma and taste is imparted prior to and on smoking in both the main stream and the side stream by the product of Example VIII.

When evaluated by a paired comparison, these cigarettes are treated in both the tobacco and the filter with the compound of Example IX are found in smoked flavored to have oriental, spicy, cinnamon-like aroma and taste nuances causing the tobacco to be "oriental" and also natural in its "oriental" character. In general, an excellent "Turkish" tobacco aroma and taste is imparted prior to and on smoking in the main stream and in the side stream by the product produced according to Example IX, supra.

What is claimed is:

1. A process for augmenting or enhancing the aroma or taste of a consumable material selected from the group consisting of smoking tobacco compositions and smoking tobacco articles comprising the step of adding to said consumable material an aroma or taste augmenting or enhancing quantity of at least one compound defined according to the structure:

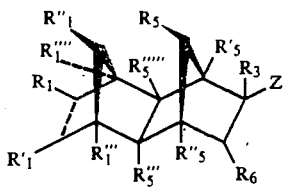

wherein the dashed line represents a carbon-carbon double bond or a carbon-carbon single bond; wherein $R_1$, $R_1'$, $R_1''$, $R_1'''$, $R_1''''$, $R_3$, $R_5$, $R_5'$, $R_5''$, $R_5'''$, $R_5''''$ and $R_6$ represent hydrogen or methyl; with the provisos:
 (i) at least four of $R_1$, $R_1'$, $R_1''$, $R_1'''$ and $R_1''''$ represents hydrogen; and
 (ii) at least four of $R_5$, $R_5'$, $R_5''$, $R_5'''$, $R_5''''$ represent hydrogen;
with Z being a moiety selected from the group consisting of:

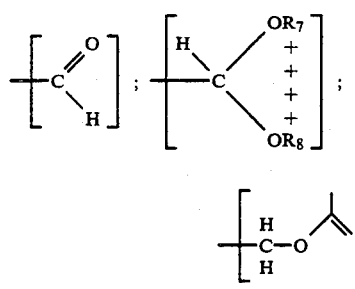

with the line:

[++++]

representing a carbon-carbon single bond or no bond at all; and $R_7$ and $R_8$ being separately $C_1$-$C_4$ lower alkyl or, taken together, being $C_2$-$C_4$ alkylene.

2. The process of claim 1 wherein the compound added to the consumable material has the structure:

3. The process of claim 1 wherein the compound added to the consumable material has the structure:

4. The process of claim 1 wherein the compound added to the consumable material has the structure:

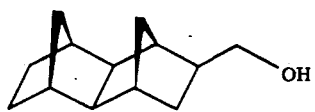

5. The process of claim 1 wherein the compound added to the consumable material has the structure:

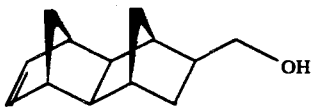

6. The process of claim 1 wherein the compound added to the consumable material has the structure:

7. The process of claim 1 wherein the substance added to the consumable material which substance is defined according to the structure:

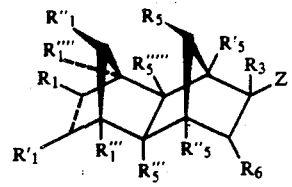

is a mixture having the structures:

and

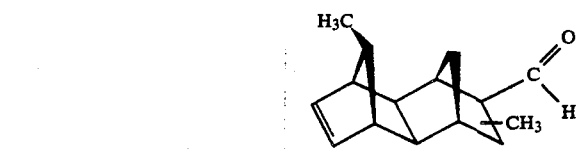

8. The process of claim 1 wherein the compound added to the consumable material has the structure:

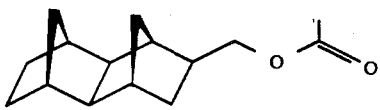

9. The process of claim 1 wherein the compound added to the consumable material has the structure:

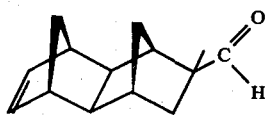
10. The process of claim 1 wherein the compound added to the consumable material has the structure:
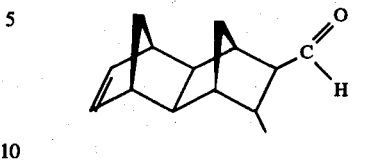
* * * * *